(12) United States Patent
Zinovik et al.

(10) Patent No.: US 12,063,970 B2
(45) Date of Patent: *Aug. 20, 2024

(54) INDUCTIVE HEATING ASSEMBLY FOR INDUCTIVE HEATING OF AN AEROSOL-FORMING SUBSTRATE

(71) Applicant: Philip Morris Products S.A., Neuchatel (CH)

(72) Inventors: Ihar Nikolaevich Zinovik, Neuchatel (CH); Irene Taurino, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 719 days.

This patent is subject to a terminal disclaimer.

(21) Appl. No.: 17/278,739

(22) PCT Filed: Sep. 24, 2019

(86) PCT No.: PCT/EP2019/075630
§ 371 (c)(1),
(2) Date: Mar. 23, 2021

(87) PCT Pub. No.: WO2020/064684
PCT Pub. Date: Apr. 2, 2020

(65) Prior Publication Data
US 2022/0030946 A1 Feb. 3, 2022

(30) Foreign Application Priority Data
Sep. 25, 2018 (EP) ..................................... 18196675

(51) Int. Cl.
*A24F 40/465* (2020.01)
*A24D 1/20* (2020.01)
(Continued)

(52) U.S. Cl.
CPC ............... *A24F 40/465* (2020.01); *A24D 1/20* (2020.01); *A24F 40/20* (2020.01); *A24F 40/57* (2020.01); *H05B 6/105* (2013.01)

(58) Field of Classification Search
CPC ......... A24D 1/20; A24F 40/20; A24F 40/465; A24F 40/57; A61M 11/042; A61M 15/06;
(Continued)

(56) References Cited

U.S. PATENT DOCUMENTS

| 3,917,970 A | 11/1975 | Sidor et al. |
| 4,256,945 A | 3/1981 | Carter et al. |

(Continued)

FOREIGN PATENT DOCUMENTS

| CA | 1115023 A | 12/1981 |
| CA | 3 097 716 A1 | 3/2017 |

(Continued)

OTHER PUBLICATIONS

Decision to Grant issued Aug. 28, 2023 in Japanese Application 2021-540921, citing documents 1-2 & 15-16 therein, 2 pages.

(Continued)

*Primary Examiner* — Quang T Van
(74) *Attorney, Agent, or Firm* — Oblon, McClelland, Maier & Neustadt, L.L.P.

(57) ABSTRACT

An inductive heating assembly is configured to inductively heat an aerosol-forming substrate to a pre-determined operating temperature, the heating assembly including an induction source configured to generate an alternating electromagnetic field; and a susceptor assembly configured to inductively heat the aerosol-forming substrate under influence of the alternating magnetic field generated by the induction source, the susceptor assembly including a first susceptor including a first susceptor material and a second susceptor including a second susceptor material having a (Continued)

Curie temperature at least 50 degrees Celsius below an operating temperature of the heating assembly. An aerosol-generating device and an aerosol-generating system include the inductive heating assembly.

19 Claims, 10 Drawing Sheets

(51) Int. Cl.
 *A24F 40/20* (2020.01)
 *A24F 40/57* (2020.01)
 *H05B 6/10* (2006.01)
(58) Field of Classification Search
 CPC .... A61M 2205/0272; A61M 2205/368; A61M 2205/8206; A61M 2205/8243; G01K 7/38; H05B 6/105; C12Q 1/6837; C12Q 1/6883; C12Q 2600/156
 USPC ....... 219/618, 628, 629, 630, 632, 634, 635, 219/643, 660, 662, 672, 211, 270; 392/386, 391, 394, 395
 See application file for complete search history.

(56) References Cited

U.S. PATENT DOCUMENTS

| | | | |
|---|---|---|---|
| 5,498,855 A | 3/1996 | Deevi et al. | |
| 5,880,439 A | 3/1999 | Deevi et al. | |
| 9,635,715 B1 | 4/2017 | Miller et al. | |
| 10,028,533 B2 | 7/2018 | Fursa et al. | |
| 10,051,890 B2 | 8/2018 | Mironov | |
| 10,499,685 B2 * | 12/2019 | Prestia | A24C 5/01 |
| 10,800,591 B1 | 10/2020 | Kalynchuk et al. | |
| 10,856,575 B2 | 12/2020 | Gill et al. | |
| 11,019,850 B2 | 6/2021 | Sebastian et al. | |
| 11,064,725 B2 | 7/2021 | Wilke et al. | |
| 11,191,298 B2 | 12/2021 | Hejazi | |
| 11,241,042 B2 | 2/2022 | Hatrick et al. | |
| 11,452,313 B2 | 9/2022 | Kaufman et al. | |
| 11,576,424 B2 * | 2/2023 | Courbat | A24F 40/44 |
| 2007/0263699 A1 | 11/2007 | Clothier et al. | |
| 2008/0006796 A1 | 1/2008 | Khatua et al. | |
| 2010/0102052 A1 | 4/2010 | Boardman | |
| 2010/0322283 A1 | 12/2010 | Clothier et al. | |
| 2014/0361007 A1 | 12/2014 | Halada et al. | |
| 2016/0021930 A1 | 1/2016 | Minskoff et al. | |
| 2016/0109115 A1 | 4/2016 | Lipowicz | |
| 2016/0150825 A1 | 6/2016 | Mironov et al. | |
| 2016/0295921 A1 | 10/2016 | Mironov et al. | |
| 2017/0027233 A1 | 2/2017 | Mironov | |
| 2017/0055587 A1 | 3/2017 | Zinovik et al. | |
| 2017/0064996 A1 | 3/2017 | Mironov | |
| 2017/0071250 A1 | 3/2017 | Mironov et al. | |
| 2017/0079325 A1 | 3/2017 | Mironov | |
| 2017/0079330 A1 | 3/2017 | Mironov et al. | |
| 2017/0119047 A1 | 5/2017 | Blandino et al. | |
| 2017/0172208 A1 | 6/2017 | Mironov | |
| 2017/0303344 A1 | 10/2017 | Laghi | |
| 2018/0184713 A1 | 7/2018 | Mironov et al. | |
| 2018/0192687 A1 | 7/2018 | Pijnenburg et al. | |
| 2018/0255833 A1 | 9/2018 | Nicolas et al. | |
| 2018/0352851 A1 | 12/2018 | Prestia et al. | |
| 2019/0008210 A1 | 1/2019 | Mironov et al. | |
| 2019/0297949 A1 | 10/2019 | Mironov et al. | |

FOREIGN PATENT DOCUMENTS

| | | |
|---|---|---|
| CA | 3 032 879 A1 | 5/2018 |
| CN | 104720121 A | 6/2015 |
| CN | 105407750 A | 3/2016 |
| CN | 106455714 A | 2/2017 |
| CN | 105263346 B | 3/2017 |
| EA | 022838 B1 | 3/2016 |
| EA | 029524 B1 | 4/2018 |
| EP | 2 021 751 A2 | 2/2009 |
| EP | 2 975 958 B1 | 3/2017 |
| EP | 3 228 198 A1 | 10/2017 |
| EP | 3 367 830 A1 | 9/2018 |
| IN | 201617024360 A | 8/2016 |
| JP | 2016-525341 A | 8/2016 |
| JP | 2017-515490 A | 6/2017 |
| JP | 2018-515113 A | 6/2018 |
| KR | 10-2017-0007262 A | 1/2017 |
| KR | 10-2018-0059918 A | 6/2018 |
| KZ | 32931 B | 7/2018 |
| RU | 2 600 912 C1 | 10/2016 |
| RU | 2 606 711 C1 | 1/2017 |
| RU | 2 606 866 C1 | 1/2017 |
| RU | 2 621 468 C1 | 6/2017 |
| RU | 2 645 205 C1 | 2/2018 |
| RU | 2 657 215 C2 | 6/2018 |
| WO | WO 2007/133813 A2 | 11/2007 |
| WO | WO 2011/120414 A1 | 10/2011 |
| WO | WO 2014/048745 A1 | 4/2014 |
| WO | WO 2015/176898 A1 | 11/2015 |
| WO | WO 2015/177045 A1 | 11/2015 |
| WO | WO 2015/177247 A1 | 11/2015 |
| WO | WO 2015/177256 A1 | 11/2015 |
| WO | WO 2015/177263 A1 | 11/2015 |
| WO | WO 2015/177264 A1 | 11/2015 |
| WO | WO 2015/177294 A1 | 11/2015 |
| WO | WO 2016/184929 A1 | 11/2016 |
| WO | WO 2017/036950 A2 | 3/2017 |
| WO | WO 2017/068337 A1 | 4/2017 |
| WO | WO 2017/072149 A1 | 5/2017 |
| WO | 2017/153443 A1 | 9/2017 |
| WO | WO 2018/041924 A1 | 3/2018 |

OTHER PUBLICATIONS

Search Report issued Jan. 16, 2023, in corresponding Russian Patent Application No. 2021108678 (with English Translation) citing documents 1, 5, 6 therein, 4 pages.
Search Report issued Jan. 17, 2023, in corresponding Russian Patent Application No. 2021108677 (with English Translation) citing documents 7-12 therein, 4 pages.
Search Report issued Jan. 18, 2023, in corresponding Russian Patent Application No. 2021111378 (with English Translation) citing documents 5,13-16, therein, 4 pages.
Search Report issued Jan. 31, 2023, in corresponding Russian Patent Application No. 2021108679 (with English Translation) citing documents 5, 6, 17 therein, 4 pages.
Search Report issued Jan. 20, 2023, in corresponding Russian Patent Application No. 2021111370 (with English Translation) citing documents 2, 3, 13, 14, 18-21 therein, 4 pages.
Office Action issued Jan. 5, 2023, in corresponding Brazilian Patent Application No. BR112021005005-1 (with English Translation), 5 pages.
Office Action issued Jan. 5, 2023, in corresponding Brazilian Patent Application No. BR112021005003-5 (with English Translation), 5 pages.
Office Action issued Sep. 4, 2023, in corresponding Japanese Patent Application No. 2021-512881 (with English Translation), citing documents 25, 26 therein, 7 pages.
Office Action issued Aug. 28, 2023, in corresponding Japanese Patent Application No. 2021-540920 (with English Translation), 5 pages.
Combined Chinese Office Action and Search Report issued Oct. 18, 2023, in corresponding Chinese Patent Application No. 201980062538.6 (with English Translation of Category of Cited Documents) citing documents 1, 2 and 27 therein, 6 pages.
Combined Chinese Office Action and Search Report issued Oct. 18, 2023, in corresponding Chinese Patent Application No. 201980062536.7 (with English Translation) citing documents 3 and 28, 29 therein, 10 pages.
Combined Chinese Office Action and Search Report issued Oct. 8, 2023, in corresponding Chinese Patent Application No. 201980062535.2 (with English Translation) citing documents 4, 30, 42 therein, 10 pages.

(56) References Cited

OTHER PUBLICATIONS

Office Action mailed Oct. 11, 2023, in co-pending U.S. Appl. No. 17/278,806.
Philippine Substantive Examination Report issued Jun. 2, 2022, in corresponding Philippine Patent Application No. 1/2021/550598, 5 pages.
International Search Report and Written Opinion issued Jan. 7, 2020, in PCT/EP2019/075632, 14 pages.
International Preliminary Report on Patentability issued Aug. 5, 2020, in PCT/EP2019/075632, 6 pages.
Engineering Technology new—ISBN 7-5326-0022-X/T.2 Encyclopedic Dictionary, by Xia Zhengnong, Shanghai Lexicographical Publishing House, Second Edition, First Printing, p. 182, published on Dec. 31, 1987.
Communication under Rule 71(3) EPC issued Apr. 11, 2022, in corresponding European Patent Application No. 19773430.4, 7 pages.
International Search report and Written Opinion issued Dec. 20, 2019 in PCT/EP2019/075630 filed Sep. 24, 2019.
Philippine Substantive Examination Report issued May 4, 2023 in Philippine Patent Application No. 1/2021/550597, citing references 1 and 2 therein, 7 pages.

* cited by examiner

INDUCTIVE HEATING ASSEMBLY FOR INDUCTIVE HEATING OF AN AEROSOL-FORMING SUBSTRATE

The present invention relates to an inductive heating assembly for inductive heating of an aerosol-forming substrate. The invention further relates to an aerosol-generating device and an aerosol-generating system comprising such an inductive heating assembly.

Aerosol-generating systems—based on inductive heating of an aerosol-forming substrate that is capable to form an inhalable aerosol upon heating—are generally known from prior art. For heating the aerosol-forming substrate, such systems may comprise an inductive heating assembly including an induction source and a susceptor. The induction source is configured for generating an alternating electromagnetic field that induces at least one of heat generating eddy currents or hysteresis losses in the susceptor. While the induction source typically is part of an aerosol-generating device, the susceptor may be either part of the device or integral part of an aerosol-generating article that is configured to be received in an aerosol-generating device including the induction source. In either case, the susceptor is arranged such as to be in thermal proximity or direct physical contact with the substrate during operation of the system.

For controlling the temperature of the substrate, susceptor assemblies have been proposed which comprise a first and a second susceptor made of different materials. The first susceptor material is optimized with regard to heat loss and thus heating efficiency. In contrast, the second susceptor material is used as temperature marker. For this, the second susceptor material is chosen such as to have a Curie temperature corresponding to a predefined operating temperature of the susceptor assembly. At its Curie temperature, the magnetic properties of the second susceptor change from ferromagnetic or ferrimagnetic to paramagnetic, accompanied by a temporary change of its electrical resistance. Thus, by monitoring a corresponding change of the electrical current absorbed by the induction source it can be detected when the second susceptor material has reached its Curie temperature and, thus, when the predefined operating temperature has been reached.

However, when monitoring the change of the electrical current absorbed by the induction source it may prove difficult to distinguish between a situation when the second susceptor material has reached its Curie temperature and a situation when a user takes a puff, in particular an initial puff, during which the electrical current shows a similar characteristic change. The change of the electrical current during a user's puff is due to a cool down of the susceptor assembly caused by air being drawn through the aerosol-generating article when a user takes a puff. The cool down effects a temporary change of the electrical resistance of the susceptor assembly. This in turn causes a corresponding change of the electrical current absorbed by the induction source. Typically, a cool down of the susceptor assembly during a user's puff is counteracted controller-wise by temporarily increasing the heating power. Yet, this controller-induced temporary increase of the heating power may disadvantageously cause an undesired overheating of the susceptor assembly in case a monitored change of the electrical current—that is actually due to the second susceptor material having reached its Curie temperature—is erroneously identified as a user's puff.

Therefore, it would be desirable to have an inductive heating assembly with the advantages of prior art solutions but without their limitations. In particular, it would be desirable to have an inductive heating assembly which allows for improved temperature control.

According to the invention there is provided an inductive heating assembly configured to inductively heat an aerosol-forming substrate to a pre-determined operating temperature. The heating assembly comprises an induction source configured to generate an alternating electromagnetic field. The heating assembly further comprises a susceptor assembly for inductively heating the aerosol-forming substrate under the influence of the alternating magnetic field generated by the induction source. The susceptor assembly comprises a first susceptor comprising a first susceptor material and a second susceptor. The second susceptor comprises a second susceptor material having a Curie temperature at least 20 degree Celsius below the operating temperature of the heating assembly.

According to the invention, it has been recognized that a temperature gap of at least 20 degree between the Curie temperature of the second susceptor material and the operating temperature of the heating assembly is sufficiently large to reliably use the Curie temperature of the second susceptor material as temperature marker for controlling the heating temperature of the aerosol-forming substrate, without the risk of being misinterpreted as a user's puff.

Preferably, the second susceptor material has a Curie temperature at least 50 degree Celsius, in particular at least 100 degree Celsius, preferably at least 150 degree Celsius, most preferably at least 200 degree Celsius below the operating temperature. Advantageously, increasing the temperature gap between the Curie temperature of the second susceptor material and the operating temperature of the heating assembly improves proper identification of the temperature marker and thus reliability of the temperature control.

The pre-determined operating temperature may be at least 300 degree Celsius, in particular at least 350 degree Celsius, preferably at least 370 degree Celsius, most preferably of at least 400 degree Celsius. These temperatures are typical operating temperatures for heating but not burning the aerosol-forming substrate.

Accordingly, the second susceptor material preferably is chosen such that it has a Curie temperature below 350 degree Celsius, in particular below 300 degree Celsius, preferably below 250 degree Celsius, most preferably below 200 degree Celsius. These values are well below typical operating temperatures used for heating the aerosol-forming substrate. Thus, proper identification of the temperature marker is ensured.

As used herein, the term "susceptor" refers to an element that is capable to convert electromagnetic energy into heat when subjected to an alternating electromagnetic field. This may be the result of hysteresis losses and/or eddy currents induced in the susceptor, depending on the electrical and magnetic properties of the susceptor material. Hysteresis losses occur in ferromagnetic or ferrimagnetic susceptors due to magnetic domains within the material being switched under the influence of an alternating electromagnetic field. Eddy currents may be induced if the susceptor is electrically conductive. In case of an electrically conductive ferromagnetic or ferrimagnetic susceptor, heat can be generated due to both, eddy currents and hysteresis losses.

According to the invention, the second susceptor material is at least ferrimagnetic or ferromagnetic having a specific Curie temperature. The Curie temperature is the temperature above which a ferrimagnetic or ferromagnetic material loses its ferrimagnetism or ferromagnetism, respectively, and becomes paramagnetic. In addition to being ferrimagnetic or ferromagnetic, the second susceptor material may be also electrically conductive.

Preferably, the second susceptor material may comprise one of mu-metal or permalloy.

While the second susceptor is mainly configured for monitoring a temperature of the susceptor assembly, the first susceptor preferably is configured for heating the aerosol-forming substrate. For this, the first susceptor may be optimized with regard to heat loss and thus heating efficiency. Accordingly, the first susceptor material may be electrically conductive and/or one of paramagnetic, ferromagnetic or ferrimagnetic. In case the first susceptor material is ferromagnetic or ferrimagnetic, the corresponding Curie temperature of the first susceptor material preferably is distinct from the Curie temperature of the second susceptor, in particular higher than any typical operating temperature mentioned above used for heating the aerosol-forming substrate. For example, the first susceptor material may have a Curie temperature of at least 400 degree Celsius, in particular of at least 500 degree Celsius, preferably of at least 600 degree Celsius.

For example, the first susceptor material may comprise one of aluminum, iron, nickel, copper, bronze, cobalt, plain-carbon steel, stainless steel, ferritic stainless steel, martensitic stainless steel, or austenitic stainless steel.

Preferably, the first susceptor material has a positive temperature coefficient of resistance, whereas the second susceptor material preferably has a negative temperature coefficient of resistance. According to the invention, it has been recognized that a susceptor assembly—comprising two susceptor materials having opposite temperature coefficients of resistance—has a resistance-over-temperature profile which includes a minimum value of resistance around a Curie temperature of the second susceptor material, for example ±5 degree Celsius around a Curie temperature of the second susceptor material. Preferably, this minimum value is a global minimum of the resistance-over-temperature profile. The minimum is caused by the opposite temperature behavior of the respective electrical resistance of the first and second susceptor material and the magnetic properties of the second susceptor material. When starting heating the susceptor assembly from room temperature, the resistance of the first susceptor material increases while the resistance of the second susceptor material decreases with increasing temperature. The overall apparent resistance of the susceptor assembly—as "seen" by an induction source used to inductively heat the susceptor assembly—is given by a combination of the respective resistance of the first and second susceptor material. When reaching the Curie temperature of the second susceptor material from below, the decrease of the resistance of the second susceptor material typically dominates the increase of the resistance of the first susceptor material. Accordingly, the overall apparent resistance of the susceptor assembly decreases in a temperature range below, in particular proximately below the Curie temperature of the second susceptor material. At the Curie temperature, the second susceptor material loses its magnetic properties. This causes an increase in the skin layer available for eddy currents in the second susceptor material, accompanied by a sudden drop down of its resistance. Thus, when further increasing the temperature of the susceptor assembly beyond the Curie temperature of the second susceptor material, the contribution of the resistance of the second susceptor material to the overall apparent resistance of the susceptor assembly becomes less or even negligible. Consequently, after having passed a minimum value around the Curie temperature of the second susceptor material, the overall apparent resistance of the susceptor assembly is mainly given by the increasing resistance of the first susceptor material. That is, the overall apparent resistance of the susceptor assembly increases again. Advantageously, the decrease and subsequent increase in the resistance-over-temperature profile around the minimum value at about the Curie temperature of the second susceptor material is sufficiently distinguishable from the temporary change of the overall apparent resistance during a user's puff. As a result, the minimum value of resistance around the Curie temperature of the second susceptor material may be reliably used as temperature marker for controlling the heating temperature of the aerosol-forming substrate, without the risk of being misinterpreted as a user's puff. Accordingly, prevention from undesired overheating of the aerosol-forming substrate is further improved.

Preferably, the first susceptor and the second susceptor are in intimate physical contact with each other. In particular, the first and second susceptor may form a unitary susceptor assembly. Thus, when heated the first and second susceptor have essentially the same temperature. Due to this, temperature control of the first susceptor by the second susceptor is highly accurate. Intimate contact between the first susceptor and the second susceptor may be accomplished by any suitable means. For example, the second susceptor may be plated, deposited, coated, cladded or welded onto the first susceptor. Preferred methods include electroplating (galvanic plating), cladding, dip coating or roll coating.

The susceptor assembly according to the present invention is preferably configured to be driven by an alternating, in particular high-frequency electromagnetic field. As referred to herein, the high-frequency electromagnetic field may be in the range between 500 kHz (kilo-Hertz) to 30 MHz (Mega-Hertz), in particular between 5 MHz (Mega-Hertz) to 15 MHz (Mega-Hertz), preferably between 5 MHz (Mega-Hertz) and 10 MHz (Mega-Hertz).

Each one of the first susceptor and the second susceptor, or the susceptor assembly may comprise a variety of geometrical configurations. At least one of the first susceptor, the second susceptor or the susceptor assembly may be one of a particulate susceptor, or a susceptor filament, or a susceptor mesh, or a susceptor wick, or a susceptor pin, or a susceptor rod, or a susceptor blade, or a susceptor strip, or a susceptor sleeve, or a susceptor cup or a cylindrical susceptor, or a planar susceptor.

As an example, at least one of the first susceptor, the second susceptor or the susceptor assembly may be one of a filament susceptor or a mesh susceptor or a wick susceptor. Such susceptors may have advantages with regard to their manufacture, their geometrical regularity and reproducibility as well as their wicking function. The geometrical regularity and reproducibility may prove advantageous in both, temperature control and controlled local heating. A wicking function may prove advantageous for use with liquid aerosol-forming substrate. In use, any of these susceptors may be in direct physical contact with the aerosol-forming substrate to be heated. For example, a filament-like first and/or second susceptor may be embedded within an aerosol-forming substrate of an aerosol-generating article. Likewise, the first and/or the second susceptor may be a mesh susceptor or wick susceptor, either as part of an aerosol-generating article which preferably comprises a liquid aerosol-forming substrate, or as part of an aerosol-generating device. In the latter configuration, the device may comprise a reservoir for a liquid aerosol-forming substrate. Alternatively, the device may be configured to receive an aerosol-generating article, in particular a cartridge, which includes a liquid aerosol-forming substrate and which is configured to engage a filament susceptor or mesh susceptor or wick susceptor of the aerosol-generating device.

At least one of the first susceptor, the second susceptor or the susceptor assembly may be a susceptor blade or a susceptor rod or a susceptor pin. Preferably, the first susceptor and the second susceptor together form a susceptor blade or a susceptor rod or a susceptor pin. For example, one of the first or the second susceptor may form a core or inner layer of a susceptor blade or a susceptor rod or a susceptor pin, whereas the respective other one of the first or second susceptor may form a jacket or envelope of the susceptor blade or susceptor rod or susceptor pin.

As susceptor blade or susceptor rod or susceptor pin, at least one of the first susceptor, the second susceptor or the susceptor assembly may be part of an aerosol-generating article, in particular may be arranged within the aerosol-forming substrate of the aerosol-generating article. One extreme end of the susceptor blade or susceptor rod or susceptor pin may tapered or pointed such as to facilitate insertion of the susceptor blade or susceptor rod or susceptor pin into the aerosol-forming substrate of the article.

Alternatively, at least one of the first susceptor, the second susceptor or the susceptor assembly—each as susceptor blade or susceptor rod or susceptor pin—may be part of an aerosol-generating device. With one of its end, in particular with a distal end, the susceptor blade or susceptor rod or susceptor pin may be arranged at, in particular attached to a bottom portion of a receiving cavity of the device. From there, the susceptor blade or susceptor rod or susceptor pin preferably extends into the inner void of the receiving cavity towards an opening of the receiving cavity. The opening of the receiving cavity preferably is located at a proximal end of the aerosol-generating device. The other end, that is, the distal free end of the susceptor blade or susceptor rod or susceptor pin may be tapered or pointed such as to allow the susceptor blade or susceptor rod or susceptor pin to readily penetrate into an aerosol-forming substrate to be heated, for example into aerosol-forming substrate arranged at a distal end portion of an aerosol-generating article.

In each case, the susceptor blade or susceptor rod or susceptor pin may have a length in a range of 8 mm (millimeter) to 16 mm (millimeter), in particular, 10 mm (millimeter) to 14 mm (millimeter), preferably 12 mm (millimeter). In case of the susceptor blade, the first susceptor and/or second susceptor, in particular the susceptor assembly may have a width, for example, in a range of 2 mm (millimeter) to 6 mm (millimeter), in particular, 4 mm (millimeter) to 5 mm (millimeter). Likewise, a thickness of a blade-shaped first susceptor and/or second susceptor, in particular of a blade-shaped susceptor assembly preferably is in a range of 0.03 mm (millimeter) to 0.15 mm (millimeter), more preferably 0.05 mm (millimeter) to 0.09 mm (millimeter).

At least one of the first susceptor, the second susceptor or the susceptor assembly may be a cylindrical susceptor or a susceptor sleeve or a susceptor cup. The cylindrical susceptor or susceptor sleeve susceptor cup may form a receiving cavity or may be circumferentially arranged around a receiving cavity of an aerosol-generating device the heating assembly may be part of. In this configuration, the first and/or second susceptor or the susceptor assembly realizes an inductive heating oven or heating chamber configured to receive the aerosol-forming substrate to be heated therein. Alternatively, at least one of the first susceptor, the second susceptor or the susceptor assembly—each as cylindrical susceptor or susceptor sleeve or susceptor cup—may surround at least a portion of the aerosol-forming substrate to be heated, thus realizing a heating oven or heating chamber. In particular, each of them may form at least a portion of a shell, wrapper, casing or housing of an aerosol-generating article.

The susceptor assembly may be a multi-layer susceptor assembly. As to this, the first susceptor and the second susceptor may form layers, in particular adjacent layers of the multi-layer susceptor assembly.

In the multi-layer susceptor assembly, the first susceptor, the second susceptor may be intimate physical contact with each other. Due to this, the temperature control of the first susceptor by the second susceptor is sufficiently accurate since the first and second susceptor have essentially the same temperature.

The second susceptor may be plated, deposited, coated, cladded or welded onto the first susceptor. Preferably, the second susceptor is applied onto the first susceptor by spraying, dip coating, roll coating, electroplating or cladding.

It is preferred that the second susceptor is present as a dense layer. A dense layer has a higher magnetic permeability than a porous layer, making it easier to detect fine changes at the Curie temperature.

The individual layers of the multi-layer susceptor assembly may be bare or exposed to the environment on a circumferential outer surface of the multi-layer susceptor assembly as viewed in any direction parallel and/or transverse to the layers. Alternatively, the multi-layer susceptor assembly may be coated with a protective coating.

The multi-layer susceptor assembly may be used to realize different geometrical configurations of the susceptor assembly.

For example, the multi-layer susceptor assembly may be an elongated susceptor strip or susceptor blade having a length in a range of 8 mm (millimeter) to 16 mm (millimeter), in particular, 10 mm (millimeter) to 14 mm (millimeter), preferably 12 mm (millimeter). A width of the susceptor assembly may be, for example, in a range of 2 mm (millimeter) to 6 mm (millimeter), in particular, 4 mm (millimeter) to 5 mm (millimeter). A thickness of the susceptor assembly preferably is in a range of 0.03 mm (millimeter) to 0.15 mm (millimeter), more preferably 0.05 mm (millimeter) to 0.09 mm (millimeter). The multi-layer susceptor blade may have a free tapered end.

As an example, the multi-layer susceptor assembly may be an elongated strip, having a first susceptor which is a strip of 430 grade stainless steel having a length of 12 mm (millimeter), a width of between 4 mm (millimeter) and 5 mm (millimeter), for example 4 mm (millimeter), and a thickness of about 50 μm (micrometer). The grade 430 stainless steel may be coated with a layer of mu-metal or permalloy as second susceptor having a thickness of between 5 μm (micrometer) and 30 μm (micrometer), for example 10 μm (micrometer).

The term "thickness" is used herein refers to dimensions extending between the top and the bottom side, for example between a top side and a bottom side of a layer or a top side and a bottom side of the multi-layer susceptor assembly. The term "width" is used herein to refer to dimensions extending between two opposed lateral sides. The term "length" is used herein to refer to dimensions extending between the front and the back or between other two opposed sides orthogonal to the two opposed lateral sides forming the width. Thickness, width and length may be orthogonal to each other.

Likewise, the multi-layer susceptor assembly may be a multi-layer susceptor rod or a multi-layer susceptor pin, in particular as described before. In this configuration, one of the first or second susceptor may form a core layer which is surrounded a surrounding layer formed by the respective other one of the first or second susceptor. Preferably, it is the first susceptor which forms surrounding layer in case the first susceptor is optimized for heating of the substrate. Thus, heat transfer to the surrounding aerosol-forming substrate is enhanced.

Alternatively, the multi-layer susceptor assembly may be a multi-layer susceptor sleeve or a multi-layer susceptor cup or cylindrical multi-layer susceptor, in particular as described before. One of the first or second susceptor may form an inner wall of the multi-layer susceptor sleeve or the multi-layer susceptor cup or the cylindrical multi-layer susceptor. The respective other one of the first or second susceptor may form an outer wall of the multi-layer susceptor sleeve or the multi-layer susceptor cup or the cylindrical multi-layer susceptor. Preferably, it is the first susceptor which forms an inner wall, in particular in case the first susceptor is optimized for heating of the substrate. As described before, the multi-layer susceptor sleeve or the multi-layer susceptor cup or the cylindrical multi-layer susceptor may surround at least a portion of the aerosol-forming substrate to be heated, in particular may form at least a portion of a shell, wrapper, casing or housing of the aerosol-generating article. Alternatively, the multi-layer susceptor sleeve or the multi-layer susceptor cup or the cylindrical multi-layer susceptor may form a receiving cavity or may be circumferentially arranged around a receiving cavity of an aerosol-generating device the heating assembly may be part of.

It may be desirable, for example, for manufacturing purposes of the aerosol-generating article that the first and second susceptors are of similar geometrical configurations, such as described above.

Alternatively, the first susceptor and the second susceptor may be of different geometrical configurations. Thus, the first and second susceptors may be tailored to their specific function. The first susceptor, preferably having a heating function, may have a geometrical configuration which presents a large surface area to the aerosol-forming substrate in order to enhance heat transfer. In contrast, the second susceptor, preferably having a temperature control function, does not need to have a very large surface area. If the first susceptor material is optimized for heating of the substrate, it may be preferred that there is no greater volume of the second susceptor material than is required to provide a detectable Curie point.

According to this aspect, the second susceptor may comprise one or more second susceptor elements. Preferably, the one or more second susceptor elements are significantly smaller than the first susceptor, that is, have a volume smaller than a volume of the first susceptor. Each of the one or more second susceptor elements may be in intimate physical contact with the first susceptor. Due to this, the first and the second susceptor have essentially the same temperature which improves accuracy of the temperature control of the first susceptor via the second susceptor serving as temperature marker.

For example, the first susceptor may be in the form of a susceptor blade or a susceptor strip or a susceptor sleeve or a susceptor cup, whereas the second susceptor material may be in the form of discrete patches that are plated, deposited, or welded onto the first susceptor material.

According to another example, the first susceptor may be of a strip susceptor or a filament susceptor or a mesh susceptor, whereas the second susceptor is a particulate susceptor. Both, the filament or mesh-like first susceptor and the particulate second susceptor may be, for example, embedded in an aerosol-generating article in direct physical contact with the aerosol-forming substrate to be heated. In this specific configuration, the first susceptor may extend within the aerosol-forming substrate through a center of the aerosol-generating article, while the second susceptor may be homogenously distributed throughout the aerosol-forming substrate.

The first and the second susceptor do not need to be in intimate physical contact with each other. The first susceptor may be a susceptor blade realizing a heating blade for penetration into an aerosol-forming substrate to be heated. Likewise, the first susceptor may be a susceptor sleeve or a susceptor cup realizing a heating oven or heating chamber. In either of these configurations, the second susceptor may be located at a different place within the heating assembly, spaced apart from but still in thermal proximity to the first susceptor.

The first and second susceptor may form different parts of the susceptor assembly. For example, the first susceptor may form a side wall portion or sleeve portion of a cup-shaped susceptor assembly, whereas the second susceptor forms a bottom portion of the cup-shaped susceptor assembly.

A least a portion of at least one of the first susceptor and the second susceptor may comprise a protective cover. Likewise, at least a portion of the susceptor assembly may comprise a protective cover. The protective cover may be formed by a glass, a ceramic, or an inert metal, formed or coated over at least a portion of the first susceptor and/or the second susceptor, or the susceptor assembly, respectively. Advantageously, the protective cover may be configured to at least one of: to avoid aerosol-forming substrate sticking to the surface of the susceptor, to avoid material diffusion, for example metal diffusion, from the susceptor materials into the aerosol-forming substrate, to improve the mechanical stiffness of the susceptor assembly. Preferably, the protective cover is electrically non-conductive.

For generating the alternating electromagnetic field, the induction source may comprise at least one inductor, preferably at least one induction coil.

The induction source may comprise a single induction coil or a plurality of induction coils. The number of induction coils may depend on the number of susceptors and/or the size and shape of the susceptor assembly. The induction coil or coils may have a shape matching the shape of the first and/or second susceptor or the susceptor assembly, respectively. Likewise, the induction coil or coils may have a shape to conform to a shape of a housing of an aerosol-generating device the heating assembly may be part of.

The at least one induction coil may be a helical coil or flat planar coil, in particular a pancake coil or a curved planar coil. Use of a flat spiral coil allows for compact design that is robust and inexpensive to manufacture. Use of a helical induction coil advantageously allows for generating a homogeneous alternating electromagnetic field. As used herein a "flat spiral coil" means a coil that is generally planar coil, wherein the axis of winding of the coil is normal to the surface in which the coil lies. The flat spiral induction can have any desired shape within the plane of the coil. For example, the flat spiral coil may have a circular shape or may have a generally oblong or rectangular shape. However, the term "flat spiral coil" as used herein covers both, coils that are planar as well as flat spiral coils that are shaped to conform to a curved surface. For example, the induction coil may be a "curved" planar coil arranged at the circumference of a preferably cylindrical coil support, for example ferrite core. Furthermore, the flat spiral coil may comprise for example two layers of a four-turn flat spiral coil or a single layer of four-turn flat spiral coil.

The first and/or second induction coil can be held within one of a housing of the heating assembly, or a main body or a housing of an aerosol-generating device which comprises the heating assembly. The first and/or second induction coil may be wound around a preferably cylindrical coil support, for example a ferrite core.

The induction source may comprise an alternating current (AC) generator. The AC generator may be powered by a power supply of the aerosol-generating device. The AC generator is operatively coupled to the at least one induction coil. In particular, the at least one induction coil may be integral part of the AC generator. The AC generator is configured to generate a high frequency oscillating current to be passed through the at least one induction coil for generating an alternating electromagnetic field. The AC current may be supplied to the at least one induction coil continuously following activation of the system or may be supplied intermittently, such as on a puff by puff basis.

Preferably, the induction source comprises a DC/AC converter connected to the DC power supply including an LC network, wherein the LC network comprises a series connection of a capacitor and the inductor.

The induction source preferably is configured to generate a high-frequency electromagnetic field. As referred to herein, the high-frequency electromagnetic field may be in the range between 500 kHz (kilo-Hertz) to 30 MHz (Mega-Hertz), in particular between 5 MHz (Mega-Hertz) to 15 MHz (Mega-Hertz), preferably between 5 MHz (Mega-Hertz) and 10 MHz (Mega-Hertz).

The heating assembly may further comprise a controller configured to control operation of the heating assembly. In particular, the controller may be configured to control operation of the induction source, preferably in a closed-loop configuration, for controlling heating of the aerosol-forming substrate to a pre-determined operating temperature. As mentioned before, the operating temperature used for heating the aerosol-forming substrate may be at least 300 degree Celsius, in particular at least 350 degree Celsius, preferably at least 370 degree Celsius, most preferably of at least 400 degree Celsius. These temperatures are typical operating temperatures for heating but not combusting the aerosol-forming substrate.

The controller may comprise a microprocessor, for example a programmable microprocessor, a microcontroller, or an application specific integrated chip (ASIC) or other electronic circuitry capable of providing control. The controller may comprise further electronic components, such as at least one DC/AC inverter and/or power amplifiers, for example a Class-D or Class-E power amplifier. In particular, the induction source may be part of the controller.

The controller may be or may be art of an overall controller of an aerosol-generating device which the heating assembly according to the present invention is part of.

The controller and at least a portion of the induction source, in particular the induction source apart from the inductor, may be arranged at a common printed circuit board. This proves particularly advantageous with regard to a compact design of the heating assembly.

The controller may be configured to determine during pre-heating of the susceptor assembly—starting at room temperature towards the operating temperature—a minimum value of an apparent resistance occurring in a temperature range of ±5 degree Celsius around the Curie temperature of the second susceptor material. Advantageously, this enables to properly identify the temperature marker about the Curie temperature of the second susceptor material. For this, the controller may be in general configured to determine from a supply voltage, in particular a DC supply voltage, and form a supply current, in particular a DC supply current, drawn from a power supply an actual apparent resistance of the susceptor assembly which in turn is indicative of the actual temperature of the susceptor assembly.

To determine an actual apparent resistance of the susceptor assembly that is indicative of the actual temperature of the susceptor assembly the controller of the heating assembly may comprise at least one of a voltage sensor, in particular a DC voltage sensor for measuring a supply voltage, in particular a DC supply voltage drawn from the power supply, or a current sensor, in particular a DC current sensor for measuring a supply current, in particular a DC supply current drawn from the power supply.

In addition, the controller may be configured to control operation of the induction source in a closed-loop configuration such that the actual apparent resistance corresponds to the determined minimum value of the apparent resistance plus a pre-determined offset value of the apparent resistance for controlling heating of the aerosol-forming substrate to the operating temperature. With regard to this aspect, control of the heating temperate preferably is based on the principles of offset locking or offset control using a pre-determined offset value of the apparent resistance to bridge the gap between the apparent resistance measured at the marker temperature and the apparent resistance at the operating temperature. Advantageously, this enables to avoid direct control of the heating temperature based on a pre-determined target value of the apparent resistant at the operating temperature, and, thus, to avoid misinterpretation of the measured resistance feature.

Furthermore, offset control of the heating temperature is more stable and reliable than a temperature control that is based on measured absolute values of the apparent resistance at the desired operating temperature. This is due to the fact that a measured absolute value of the apparent resistance as determined from a supply voltage and a supply current depends on various factors, such as for example the resistance of the electrical circuitry of the induction source and various contact resistances. Such factors are prone to environmental effects and may vary over time and/or between different induction sources and susceptor assemblies of the same type, conditionally on manufacturing. Advantageously, such effects substantially cancel out for the value of the difference between two measured absolute values of the apparent resistance. Accordingly, using an offset value of the apparent resistance for controlling the temperature is less prone to such adverse effects and variations.

The offset value of the apparent resistance for controlling the heating temperature of the aerosol-forming substrate to the operating temperature may be pre-determined by means of a calibration measurement, for example during manufacturing of the device.

Preferably, the minimum value at about the Curie temperature of the second susceptor material is a global minimum of the resistance-over-temperature profile.

As used herein, the term "starting from room temperature" preferably means that the minimum value at about the Curie temperature of the second susceptor material occurs in the resistance-over-temperature profile during pre-heating, that is a heat-up of the susceptor assembly from room temperature towards an operating temperature at which the aerosol-forming substrate is to be heated.

As used herein, room temperature may correspond to a temperature in a range between 18 degree Celsius and 25 degree Celsius, in particular to a temperature of 20 degree Celsius.

The heating assembly may comprise a power supply, in particular a DC power supply configured to provide a DC supply voltage and a DC supply current to the induction source. Preferably, the power supply is a battery such as a lithium iron phosphate battery. As an alternative, the power supply may be another form of charge storage device such as a capacitor. The power supply may require recharging, that is, the power supply may be rechargeable. The power supply may have a capacity that allows for the storage of enough energy for one or more user experiences. For example, the power supply may have sufficient capacity to allow for the continuous generation of aerosol for a period of around six minutes or for a period that is a multiple of six minutes. In another example, the power supply may have sufficient capacity to allow for a predetermined number of puffs or discrete activations of the induction source. The power supply may be an overall power supply of an aerosol-generating device the heating assembly according to the present invention is part of.

According to the invention, there is also provided an aerosol-generating device for generating an aerosol by heating an aerosol-forming substrate. The device comprises a receiving cavity for receiving the aerosol-forming substrate to be heated. The device further comprises an inductive heating assembly according to the invention and as described herein for inductively heating the aerosol-forming substrate within the receiving cavity.

As used herein, the term "aerosol-generating device" is used to describe an electrically operated device that is capable of interacting with at least one aerosol-forming substrate, in particular with an aerosol-forming substrate provided within an aerosol-generating article, such as to generate an aerosol by heating the substrate. Preferably, the aerosol-generating device is a puffing device for generating an aerosol that is directly inhalable by a user thorough the user's mouth. In particular, the aerosol-generating device is a hand-held aerosol-generating device.

As used herein, the term "aerosol-forming substrate" relates to a substrate capable of releasing volatile compounds that can form an aerosol upon heating the aerosol-forming substrate. The aerosol-forming substrate is part of the aerosol-generating article. The aerosol-forming substrate may be a solid or, preferably, a liquid aerosol-forming substrate. In both cases, the aerosol-forming substrate may comprise at least one of solid and liquid components. The aerosol-forming substrate may comprise a tobacco-containing material containing volatile tobacco flavor compounds, which are released from the substrate upon heating. Alternatively or additionally, the aerosol-forming substrate may comprise a non-tobacco material. The aerosol-forming substrate may further comprise an aerosol former. Examples of suitable aerosol formers are glycerine and propylene glycol. The aerosol-forming substrate may also comprise other additives and ingredients, such as nicotine or flavourants. The aerosol-forming substrate may also be a paste-like material, a sachet of porous material comprising aerosol-forming substrate, or, for example, loose tobacco mixed with a gelling agent or sticky agent, which could include a common aerosol former such as glycerine, and which is compressed or molded into a plug.

The receiving cavity may be embedded in a housing of the aerosol-generating device.

As described above, the aerosol-generating device may comprise an overall controller for controlling operation of the device. The overall controller may comprise or may include a controller of the heating assembly.

As further described above, the aerosol-generating device may also comprise a power supply, in particular a DC power supply, such as a battery. In particular, the power supply may be an overall power supply of the aerosol-generating device that is used, inter alia, to provide a DC supply voltage and a DC supply current to the induction source of the heating assembly.

The aerosol-generating device may comprise a main body which preferably includes at least one of the induction source, the at least one induction coil, the controller, the power supply and at least a portion of the receiving cavity.

In addition to the main body, the aerosol-generating device may further comprise a mouthpiece, in particular in case the aerosol-generating article to be used with the device does not comprise a mouthpiece. The mouthpiece may be mounted to the main body of the device. The mouthpiece may be configured to close the receiving cavity upon mounting the mouthpiece to the main body. For attaching the mouthpiece to the main body, a proximal end portion of the main body may comprise a magnetic or mechanical mount, for example, a bayonet mount or a snap-fit mount, which engages with a corresponding counterpart at a distal end portion of the mouthpiece. In case the device does not comprise a mouthpiece, an aerosol-generating article to be used with the aerosol-generating device may comprise a mouthpiece, for example a filter plug.

The aerosol-generating device may comprise at least one air outlet, for example, an air outlet in the mouthpiece (if present).

Preferably, the aerosol-generating device comprises an air path extending from the at least one air inlet through the receiving cavity, and possibly further to an air outlet in the mouthpiece, if present. Preferably, the aerosol-generating device comprises at least one air inlet in fluid communication with the receiving cavity. Accordingly, the aerosol-generating system may comprise an air path extending from the at least one air inlet into the receiving cavity, and possibly further through the aerosol-forming substrate within the article and a mouthpiece into a user's mouth.

Further features and advantages of the aerosol-generating device according to the present invention have been described with regard to the heating assembly and will not be repeated.

According to the invention, there is also provided an aerosol-generating system. The system comprises an aerosol-generating device, an aerosol-generating article for use with the aerosol-generating device, and an inductive heating assembly according to the invention and as described herein. The induction source of the heating assembly is part of the aerosol-generating device. The first susceptor of the susceptor assembly is part of the aerosol-generating article, whereas the second susceptor of the susceptor assembly is either part of the aerosol-generating article or part of the aerosol-generating device.

Advantageously, the first susceptor—as part of the aerosol-generating article as—may be configured for heating the aerosol-forming substrate. For this, the first susceptor may be optimized with regard to heat loss and thus heating efficiency. For example, the first susceptor may be a susceptor strip, a susceptor blade, a susceptor rod, a susceptor pin, a susceptor mesh, a susceptor filament or a particulate susceptor arranged with the aerosol-forming substrate of the aerosol-generating article.

In contrast, the second susceptor may be mainly configured for monitoring the temperature of the susceptor assembly. For this, the second susceptor may be either part of, in particular arranged in the aerosol-generating article or the aerosol-generating device. In either configuration, when the article is used with, in particular coupled to the device, the second susceptor preferably is arranged in thermal proximity with or even thermal contact with the first susceptor and/or the aerosol-forming substrate. Advantageously, this ensures that the second susceptor substantially has the same temperature as the first susceptor and/or the aerosol-forming substrate during operation of the aerosol-generating system. Thus, thus proper and accurate temperature controlled may be achieved. For example, the second susceptor may be arranged at an inner wall of a receiving cavity of the aerosol-generating device.

If present, a controller of the heating assembly may be part of, in particular arranged in the aerosol-generating device. Preferably, a controller of the aerosol-generating device may include or may be a controller of the heating assembly.

Likewise, if present, a power supply of the heating assembly may be part of, in particular arranged in the aerosol-generating device. Preferably, a power supply of the aerosol-generating device may include or may be a power supply of the heating assembly.

The aerosol-generating device may comprise a receiving cavity for receiving at least a portion of the aerosol-generating article.

As used herein, the term "aerosol-generating article" refers to an article comprising at least one aerosol-forming substrate that, when heated, releases volatile compounds that can form an aerosol. Preferably, the aerosol-generating article is a heated aerosol-generating article. That is, an aerosol-generating article preferably comprises at least one aerosol-forming substrate that is intended to be heated rather than combusted in order to release volatile compounds that can form an aerosol. The aerosol-generating article may be a consumable, in particular a consumable to be discarded after a single use. The aerosol-generating article may be a tobacco article. For example, the article may be a cartridge including a liquid or solid aerosol-forming substrate to be heated. Alternatively, the article may be a rod-shaped article, in particular a tobacco article, resembling conventional cigarettes and including a solid aerosol-forming substrate.

Preferably, the aerosol-generating article has a circular or an elliptical or an oval or a square or a rectangular or a triangular or a polygonal cross-section.

In addition to the aerosol-forming substrate and the susceptor assembly, the article may further comprise different elements.

In particular, the article may comprise a mouthpiece. As used herein, the term "mouthpiece" means a portion of the article that is placed into a user's mouth in order to directly inhale an aerosol from the article. Preferably, the mouthpiece comprises a filter.

Furthermore, the article may comprise a casing, in particular a tubular wrapper, surrounding at least a portion of the aerosol-forming substrate. The wrapper may comprise the susceptor assembly. Advantageously, this allows for a homogeneous and symmetrical heating of the aerosol-forming substrate surrounded by the susceptor assembly.

In particular with regard to an aerosol-generating article having a rod-shape article resembling conventional cigarettes and/or comprising a solid aerosol-forming substrate, the article may further comprise: a support element having a central air passage, an aerosol-cooling element, and a filter element. The filter element preferably serves as a mouthpiece. In particular, the article may comprise a substrate element which comprises the aerosol-forming substrate and the susceptor assembly in contact with the aerosol-forming substrate. Any one or any combination of these elements may be arranged sequentially to the aerosol-forming rod segment. Preferably, the substrate element is arranged at a distal end of the article. Likewise, the filter element preferably is arranged at a proximal end of the article. Furthermore, these elements may have the same outer cross-section as the aerosol-forming rod segment.

Furthermore, the article may comprise a casing or a wrapper surrounding at least a portion of the aerosol-forming substrate. In particular, the article may comprise a wrapper surrounding at least a portion of the different segments and elements mentioned above such as to keep them together and to maintain the desired cross-sectional shape of the article.

The casing or wrapper may comprise at least the first susceptor or both, the first and the second susceptor of the susceptor assembly. Advantageously, this allows for a homogeneous and symmetrical heating of the aerosol-forming substrate surrounded by the first susceptor or the susceptor assembly.

Preferably, the casing or wrapper forms at least a portion of the outer surface of the article. The casing may form a cartridge including a reservoir that contains the aerosol-forming substrate, for example a liquid aerosol-forming substrate. The wrapper may be a paper wrapper, in particular a paper wrapper made of cigarette paper. Alternatively, the wrapper may be a foil, for example made of plastics. The wrapper may be fluid permeable such as to allow vaporized aerosol-forming substrate to be released from the article, or to allow air to be drawn into the article through its circumference. Furthermore, the wrapper may comprise at least one volatile substance to be activated and released from the wrapper upon heating. For example, the wrapper may be impregnated with a flavoring volatile substance.

Further features and advantages of the aerosol-generating system according to the present invention have been described with regard to the aerosol-generating device and the heating assembly and will not be repeated.

The invention will be further described, by way of example only, with reference to the accompanying drawings, in which.

Figure 1:
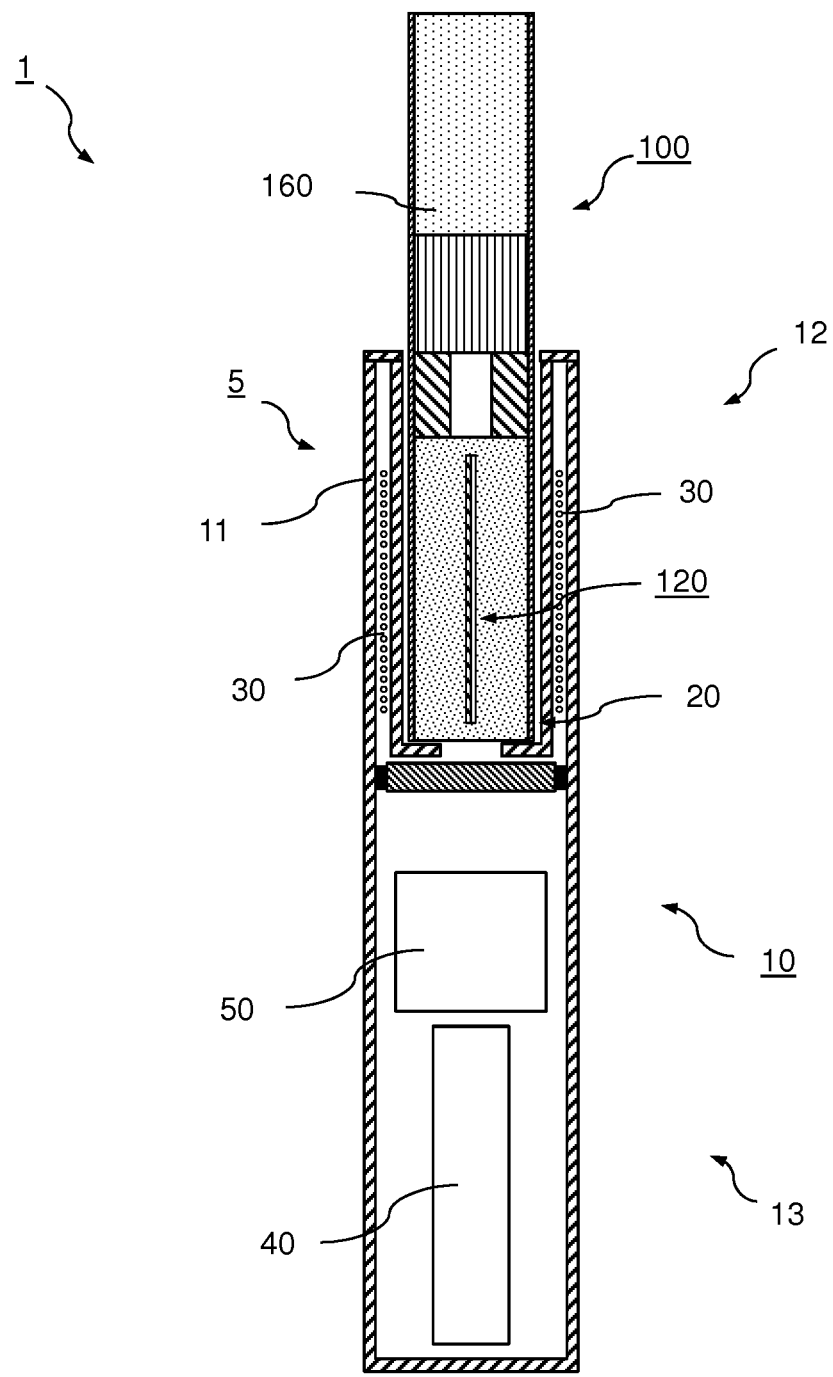
FIG. 1 is a schematic illustration of an aerosol-generating system comprising an inductively heating aerosol-generating device and an aerosol-generating article, wherein the system comprises a heating assembly according to a first exemplary embodiment of the present invention.

FIG. 1 schematically illustrates a first exemplary embodiment of an aerosol-generating system 1 according to the present invention. The system 1 comprises an aerosol-generating device 10 according to the invention as well as an aerosol-generating article 100 that is configured for use with the device and that comprises an aerosol-forming substrate to be heated.

Figure 2:
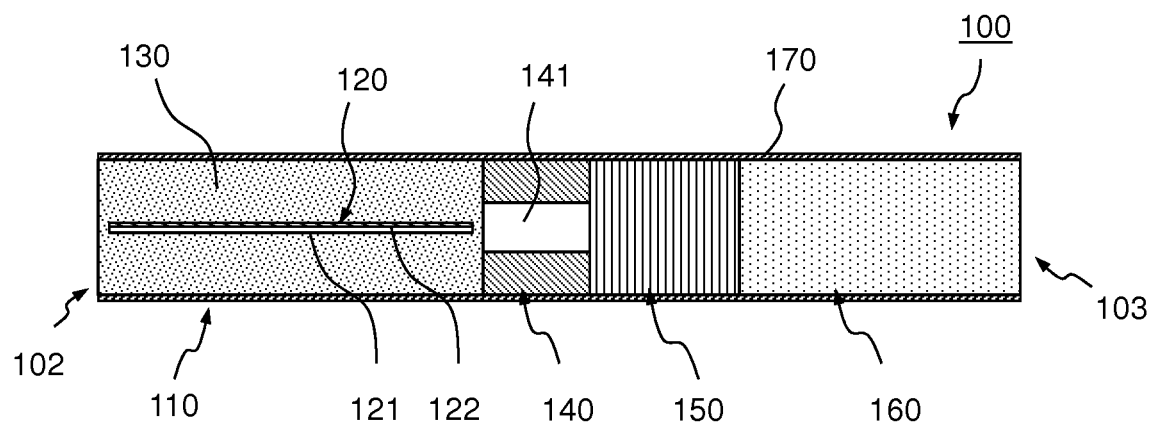
FIG. 2 is a schematic illustration of the inductively heatable aerosol-generating article according to FIG. 1.

FIG. 2 shows further details of the aerosol-generating article 100, the aerosol-generating article 100 substantially has a rod-shape and comprises four elements sequentially arranged in coaxial alignment: an aerosol-forming rod segment 110 comprising a susceptor assembly 120 and an aerosol-forming substrate 130, a support element 140 having a central air passage 141, an aerosol-cooling element 150, and a filter element 160 which serves as a mouthpiece. The aerosol-forming rod segment 110 is arranged at a distal end 102 of the article 100, whereas the filter element 160 is arranged at a distal end 103 of the article 100. Each of these four elements is a substantially cylindrical element, all of them having substantially the same diameter. In addition, the four elements are circumscribed by an outer wrapper 170 such as to keep the four elements together and to maintain the desired circular cross-sectional shape of the rod-like article 100. The wrapper 170 preferably is made of paper. Further details of the article, in particular of the four elements—apart from the specifics of the susceptor assembly 120 within the rod segment 110—are disclosed in WO 2015/176898 A1.

With reference to FIG. 1, the aerosol-generating device 10 comprises a cylindrical receiving cavity 20 defined within a proximal portion 12 of the device 10 for receiving a least a distal portion of the article 100 therein. The device 10 further comprises an induction source including an induction coil 30 for generating an alternating, in particular high-frequency electromagnetic field. In the present embodiment, the induction coil 30 is a helical coil circumferentially surrounding the cylindrical receiving cavity 20. The coil 30 is arranged such that the susceptor assembly 120 of the aerosol-generating article 100 experiences the electromagnetic field upon engaging the article 100 with the device 10. Thus, when activating the induction source, the susceptor assembly 120 heats up due to eddy currents and/or hysteresis losses that are induced by the alternating electromagnetic field, depending on the magnetic and electric properties of the susceptor materials of the susceptor assembly 120. The susceptor assembly 120 is heated until reaching an operating temperature sufficient to vaporize the aerosol-forming substrate 130 surrounding the susceptor assembly 120 within the article 100.

Within a distal portion 13, the aerosol-generating device 10 further comprises a DC power supply 40 and a controller 50 (illustrated in FIG. 1 schematically only) for powering and controlling the heating process. Electronic-wise, the induction source—apart from the induction coil 30—preferably is at least partially integral part of the controller 50.

Both, the induction source—as part of the device 10—and the susceptor assembly 120—as part of the aerosol-generating article 100—constitute the essential parts of an inductive heating assembly 5 according to the present invention.

Figure 3:
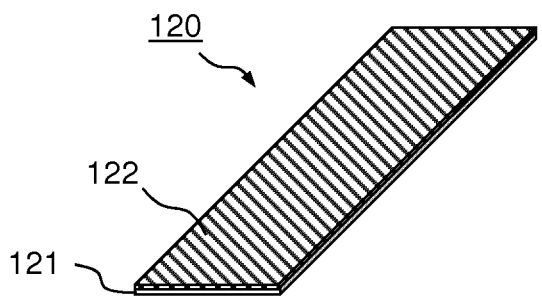
FIG. 3 is a perspective view of the susceptor assembly of the aerosol-generating article according to FIG. 1 and FIG. 2.

FIG. 3 shows a detail view of the susceptor assembly 120 used within the aerosol-generating article shown in FIG. 1 and FIG. 2. According to the invention, the susceptor assembly 120 comprises a first susceptor 121 and a second susceptor 122. The first susceptor 121 comprises a first susceptor material having a positive temperature coefficient of resistance, whereas the second susceptor 122 comprises a second ferromagnetic or ferrimagnetic susceptor material having a negative temperature coefficient of resistance. Due to the first and second susceptor materials having opposite temperature coefficients of resistance and due to the magnetic properties of the second susceptor material, the susceptor assembly 120 has a resistance-over-temperature profile which includes a minimum value of resistance around the Curie temperature of the second susceptor material.

Figure 4:
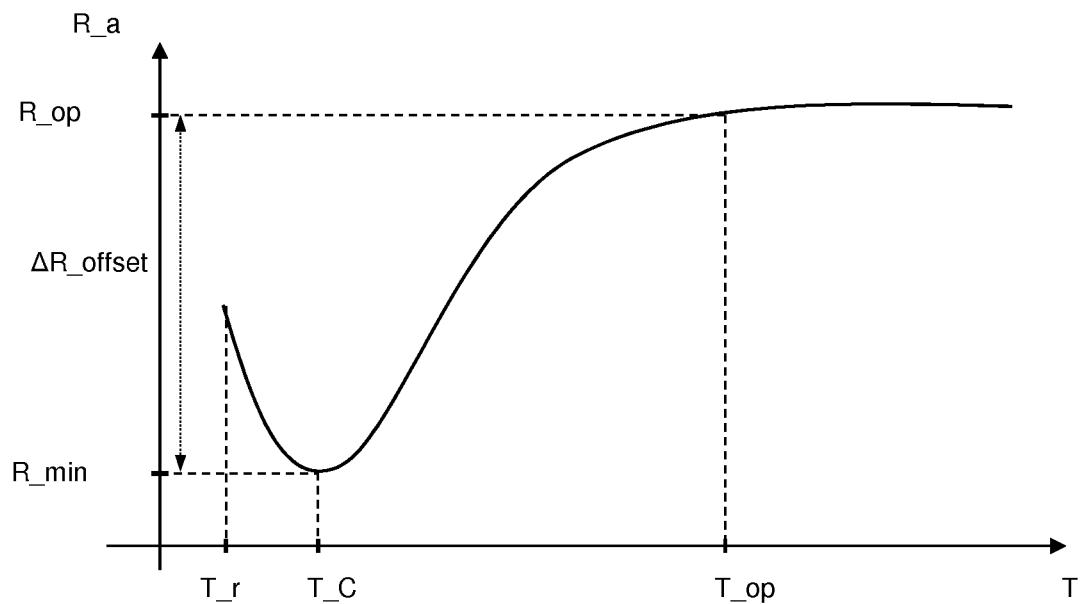
FIG. 4 is a diagram schematically illustrating the resistance-over-temperature profile of a susceptor assembly according to the present invention.

A corresponding resistance-over-temperature profile is shown in FIG. 4. When starting heating the susceptor assembly 120 from room temperature T_R, the resistance of the first susceptor material increases while the resistance of the second susceptor material decreases with increasing temperature T. The overall apparent resistance R_a of the susceptor assembly 120—as "seen" by the induction source of the device 10 used to inductively heat the susceptor assembly 120—is given by a combination of the respective resistance of the first and second susceptor material. When reaching the Curie temperature T_C of the second susceptor material from below, the decrease of the resistance of the second susceptor material typically dominates the increase of the resistance of the first susceptor material. Accordingly, the overall apparent resistance R_a of the susceptor assembly 120 decreases in a temperature range below, in particular proximately below the Curie temperature T_C of the second susceptor material. At the Curie temperature T_C, the second susceptor material loses its magnetic properties. This causes an increase in the skin layer available for eddy currents in the second susceptor material, accompanied by a sudden drop down of its resistance. Thus, when further increasing the temperature T of the susceptor assembly 120 beyond the Curie temperature T_C of the second susceptor material, the contribution of the resistance of the second susceptor material to the overall apparent resistance R_a of the susceptor assembly 120 becomes less or even negligible. Consequently, after having passed the minimum value R_min around the Curie temperature T_C of the second susceptor material, the overall apparent resistance R_a of the susceptor assembly 120 is mainly given by the increasing resistance of the first susceptor material. That is, the overall apparent resistance R_a of the susceptor assembly 120 again increases towards the operating resistance R_op at the operating temperature T_op. Advantageously, the decrease and subsequent increase in the resistance-over-temperature profile around the minimum value R_min at about the Curie temperature T_C of the second susceptor material is sufficiently distinguishable from the temporary change of the overall apparent resistance during a user's puff. As a result, the minimum value of resistance R_a around the Curie temperature T_C of the second susceptor material may be reliably used as temperature marker for controlling the heating temperature of the aerosol-forming substrate, without the risk of being misinterpreted as a user's puff. Accordingly, the aerosol-forming substrate can be effectively prevented from undesired overheating.

For controlling the heating temperature of the aerosol-forming substrate to correspond to the desired operating temperature T_op, the controller 50 of the device 10 shown in FIG. 1 is configured to control operation of the induction source in a closed-loop off-set configuration such as to keep the actual apparent resistance at a value which corresponds to the determined minimum value R_min of the apparent resistance R_a plus a pre-determined offset value ΔR_offset. The offset value ΔR_offset bridges the gap between the apparent resistance R_min measured at the marker temperature T_C and the operating resistance R_op at the operating temperature T_op. Advantageously, this enables to avoid direct control of the heating temperature based on a pre-determined target value of the apparent resistant at the operating temperature T_op. Also, offset control of the heating temperature is more stable and reliable than a temperature control that is based on measured absolute values of the apparent resistance at the desired operating temperature.

When the actual apparent resistance is equal to or exceeds the determined minimum value of the apparent resistance plus the pre-determined offset value of the apparent resistance, the heating proses may be stopped by interrupting generation of the alternating electromagnetic field, that is, by switching off the induction source or at least by reducing the output power of the induction source. When the actual apparent resistance is below the determined minimum value of the apparent resistance plus the pre-determined offset value of the apparent resistance, the heating proses may be resumed by resuming generation of the alternating electromagnetic field, that is, by switching on again the induction source or by re-increasing the output power of the induction source.

In the present embodiment, the operating temperature of is about 370 degree Celsius. This temperature is a typical operating temperature for heating but not combusting the aerosol-forming substrate. To ensure a sufficiently large temperature gap of at least 20 degrees Celsius between the marker temperature at the Curie temperature T_C of the second susceptor material and the operating temperature T_op, the second susceptor material is chosen such as to have a Curie temperature below 350 degree Celsius.

As shown in FIG. 3, the susceptor assembly 120 within the article of FIG. 2 is a multi-layer susceptor assembly, more particular a bi-layer susceptor assembly. It comprises a first layer constituting the first susceptor 121, and a second layer constituting the second susceptor 122 that is arranged upon and intimately coupled to the first layer. While the first susceptor 121 is optimized with regard to heat loss and thus heating efficiency, the second susceptor 122 primarily is a functional susceptor used as temperature marker, as described above. The susceptor assembly 120 is in the form of an elongate strip having a length L of 12 millimeter and a width W of 4 millimeter, that is, both layers have a length L of 12 millimeter and a width W of 4 millimeter. The first susceptor 121 is a strip made of stainless steel having a Curie temperature in excess of 400° C., for example grade 430 stainless steel. It has a thickness of about 35 micrometer. The second susceptor 122 is a strip of mu-metal or permalloy having a Curie temperature below the operating temperature. It has a thickness of about 10 micrometer. The susceptor assembly 120 is formed by cladding the second susceptor strip to the first susceptor strip.

Figure 5:
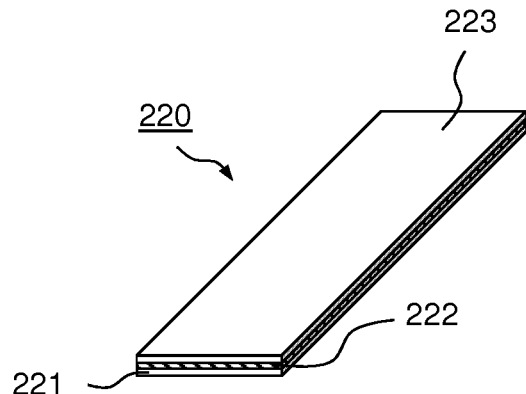
FIG. 5-7 show alternative embodiments of a susceptor assembly for use with the article according to FIG. 1 and FIG. 2.

FIG. 5 shows an alternative embodiment of a strip-shaped susceptor assembly 220 which is similar to the embodiment of the susceptor assembly 120 shown in FIGS. 1 and 2. In contrast to the latter, the susceptor assembly 220 according to FIG. 5 is a three-layer susceptor assembly which—in addition to a first and a second susceptor 221, 222 forming a first and a second layer, respectively—comprises a third susceptor 223 that forms a third layer. All three layers are arranged on top of each other, wherein adjacent layers are intimately coupled to each other. The first and second susceptors 221, 222 of the three-layer susceptor assembly shown in FIG. 5 are identical to the first and a second susceptors 121, 122 of the bi-layer susceptor assembly 120 shown in FIGS. 1 and 2. The third susceptor 223 is identical to the first susceptor 221. That is, the third layer 223 comprises the same material as the first susceptor 221. Also, the layer thickness of the third susceptor 223 is equal to the layer thickness of the first susceptor 221. Accordingly, the thermal expansion behavior of the first and third susceptor 221, 223 is substantially the same. Advantageously, this provides a highly symmetric layer structure showing essentially no out-of-plane deformations. In addition, the three-layer susceptor assembly according to FIG. 5 provides a higher mechanical stability.

Figure 6:
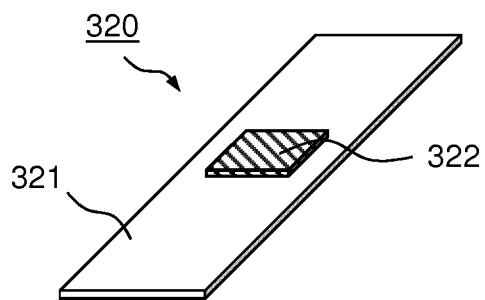

FIG. 6 shows another embodiment of a strip-shaped susceptor assembly 320 which may be alternatively used within the article of FIG. 2 instead of the bi-layer susceptor 120. The susceptor assembly 320 according to FIG. 6 is formed from a first susceptor 321 that is intimately coupled to a second susceptor 322. The first susceptor 321 is a strip of grade 430 stainless steel having dimensions of 12 millimeter by 4 millimeter by 35 micrometer. As such, the first susceptor 321 defines the basic shape of the susceptor assembly 320. The second susceptor 322 is a patch of mu-metal or permalloy of dimensions 3 millimeter by 2 millimeter by 10 micrometer. The patch-shaped second susceptor 322 is electroplated onto the strip-shaped first susceptor 321. Though the second susceptor 322 is significantly smaller than the first susceptor 321, it is still sufficient to allow for accurate control of the heating temperature. Advantageously, the susceptor assembly 320 according to FIG. 6 provides significant savings in second susceptor material. In further embodiments (not shown), there may be more than one patch of the second susceptor located in intimate contact with the first susceptor.

Figure 7:
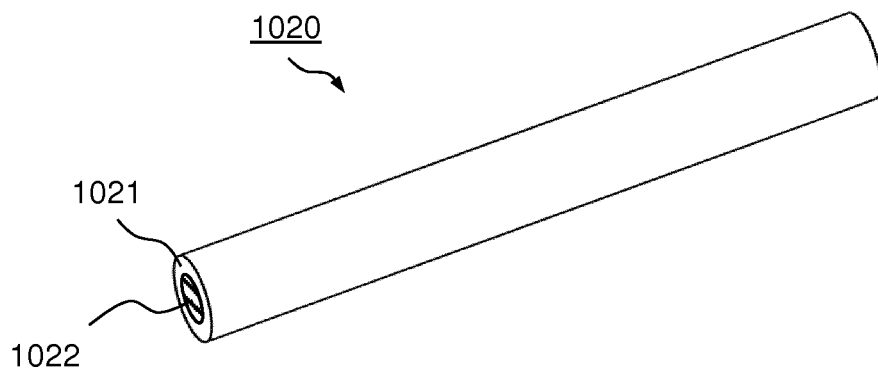

FIG. 7 shows yet another embodiment of a susceptor assembly 1020 for use with the article shown in FIG. 1 and FIG. 2. According to this embodiment, the susceptor assembly 1020 forms a susceptor rod. The susceptor rod is cylindrical having a circular cross-section. Preferably, the susceptor rod is centrally arranged within the aerosol-forming substrate such as to extend the length axis of the article shown in FIG. 2. As can be seen at one of its end faces, the susceptor assembly 1020 comprises an inner core susceptor which forms the second susceptor 1022 according to the present invention. The core susceptor is surrounded by jacket susceptor which forms the first susceptor 1021 according to the present invention. As the first susceptor 1021 preferably has a heating function, this configuration proves advantageous with regard to a direct heat transfer to the surrounding aerosol-forming substrate. In addition, the cylindrical shape of the susceptor pin provides a very symmetric heating profile which may be advantageous with regard to a rod-shaped aerosol-generating article.

Figure 8:
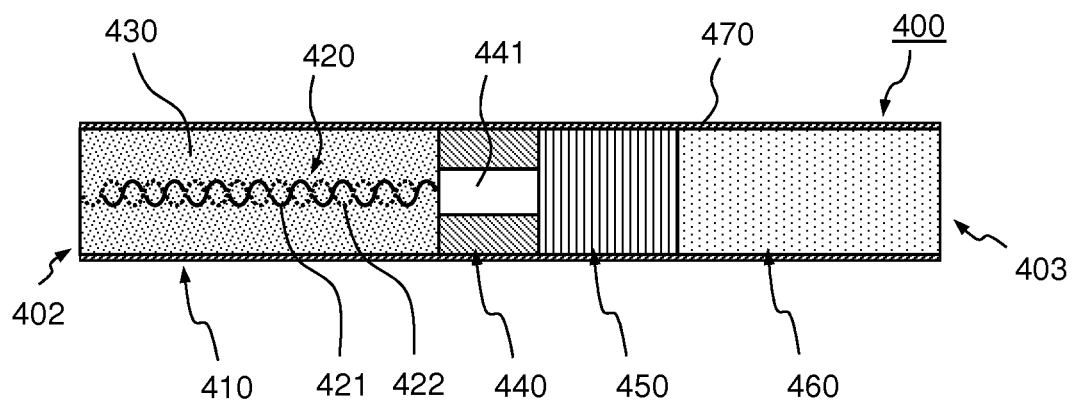
FIG. 8-10 show aerosol-generating articles for use with the device according to FIG. 1 which include further alternative embodiments of susceptor assemblies.
Figure 9:
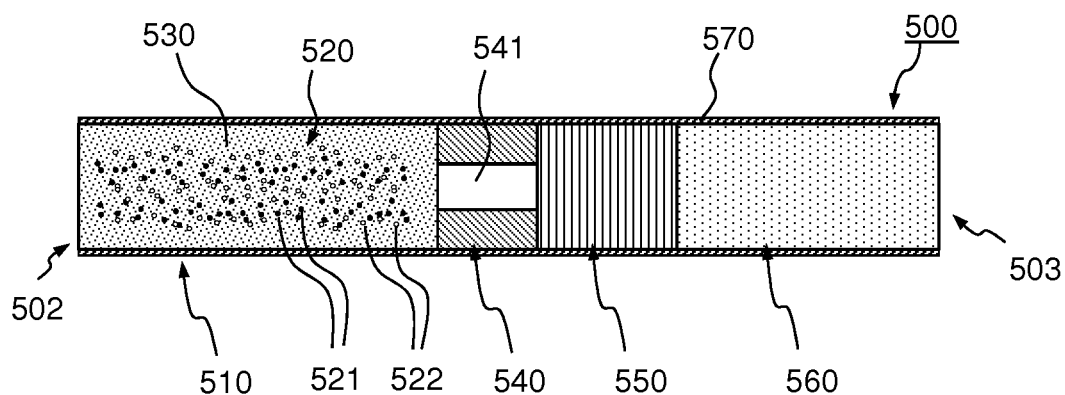
Figure 10:
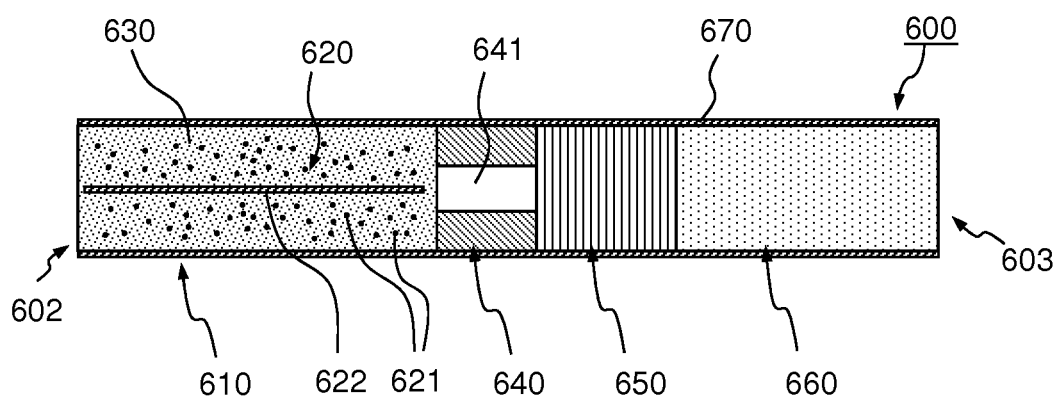

FIG. 8-10 schematically illustrate different aerosol-generating articles 400, 500, 600 comprising further embodiments a susceptor assembly that is part of a heating assembly according to the present invention. The articles 400, 500, 600 are very similar to the article 100 shown in FIGS. 1 and 2, in particular with regard to the general setup of the article. Therefore, like or identical features are denoted with the same reference numerals as in FIGS. 1 and 2, yet incremented by 300, 400 and 500, respectively.

In contrast to the article 100 shown in FIGS. 1 and 2, the aerosol-generating article 400 according to FIG. 8 comprises a filament susceptor assembly 420. That is, the first and the second susceptor 421, 422 are filaments which are twisted with each other such as to form twisted filament pair. The filament pair is centrally arranged within the aerosol-forming substrate 430 in direct contact with the substrate 430. The filament pair substantially extends along the length extension of the article 400. The first susceptor 421 is a filament made of ferromagnetic stainless steel and thus mainly has a heating function. The second susceptor 422 is filament made of mu-metal or permalloy and thus mainly serves as temperature marker.

The aerosol-generating article 500 according to FIG. 9 comprises a particulate susceptor assembly 520. Both, the first susceptor 521 and the second susceptor 522 include a plurality of susceptor particles spread within the aerosol-forming substrate 530 of the article 500. Thus, the susceptor particles are in direct physical contact with the aerosol-forming substrate 530. The susceptor particles of the first susceptor 521 are made of ferromagnetic stainless steel and thus mainly serve to heat the surrounding aerosol-forming substrate 530. In contrast, the susceptor particles of the second susceptor 422 are made of mu-metal or permalloy and thus mainly serve as temperature marker.

The aerosol-generating article 600 according to FIG. 10 comprises a susceptor assembly 600 including a first susceptor 621 and a second susceptor 622 that are of different geometrical configurations. The first susceptor 621 is a particulate susceptor comprising a plurality of susceptor particles spread in the aerosol-forming substrate 630. Due to its particulate nature, the first susceptor 621 presents a large surface area to the surrounding aerosol-forming substrate 630 which advantageously enhances heat transfer. Accordingly, the particulate configuration of the first susceptor 621 is specifically chosen with regard to a heating function. In contrast, the second susceptor 622 primarily has a temperature control function, and therefore does not need to have a very large surface area. Accordingly, the second susceptor 622 of the present embodiment is a susceptor strip extending within the aerosol-forming substrate 630 through a center of the aerosol-generating article 600.

Figure 11:
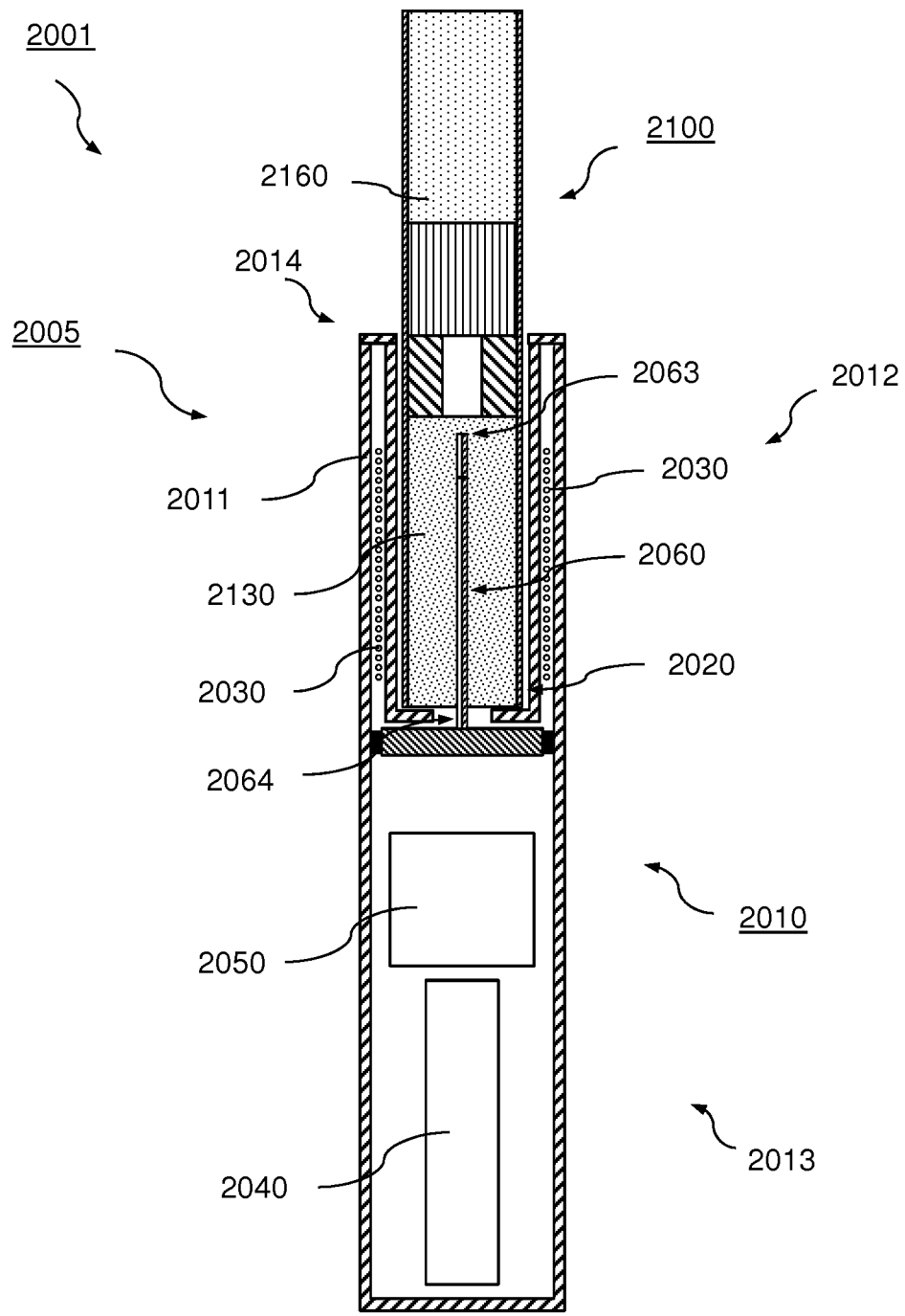
FIG. 11 is a schematic illustration of another aerosol-generating system comprising a heating assembly according to a second exemplary embodiment of the present invention.

FIG. 11 schematically illustrates a second exemplary embodiment of an aerosol-generating system 2001 according to the present invention. The system 2001 is very similar to the system 1 shown in FIG. 1, apart from the susceptor assembly. Therefore, like or identical features are denoted with the same reference numerals as in FIGS. 1 and 2, yet incremented by 2000. In contrast to the embodiment shown in FIG. 1, the susceptor assembly 2060 of the heating assembly 2005 according to the embodiment of FIG. 11 is part of the aerosol-generating device 2010.

Accordingly, the aerosol-generating article 2100 does not comprise any susceptor assembly. Hence, the article 2100 basically corresponds to the article 100 shown in FIGS. 1 and 2, yet without the susceptor assembly.

Likewise, the aerosol-generating device 2010 of FIG. 11 basically corresponds to the device 10 shown in FIG. 1. In contrast to the latter, the device 2010 comprises all parts of a heating assembly 2005 according to the present invention. That is, the device 2010 comprises an induction source including a helical induction coil 2030 that is circumferentially surrounding the cylindrical receiving cavity 2020. In addition, the device further comprises a susceptor assembly 2060 that is arranged within the receiving cavity such as to experience the electromagnetic field generated by the induction coil 2030.

The susceptor assembly 2060 is a susceptor blade. With its distal end 2064, the susceptor blade 2060 is arranged at a bottom portion of the receiving cavity 2020 of the device 2010. From there, the susceptor blade extends into the inner void of the receiving cavity 2020 towards an opening of the receiving cavity 2020. The opening of the receiving cavity 2020 is located at a proximal end 2014 of the aerosol-generating device 2010, thus allowing the aerosol-generating article 2100 to be inserted into the receiving cavity 2020.

Figure 12:
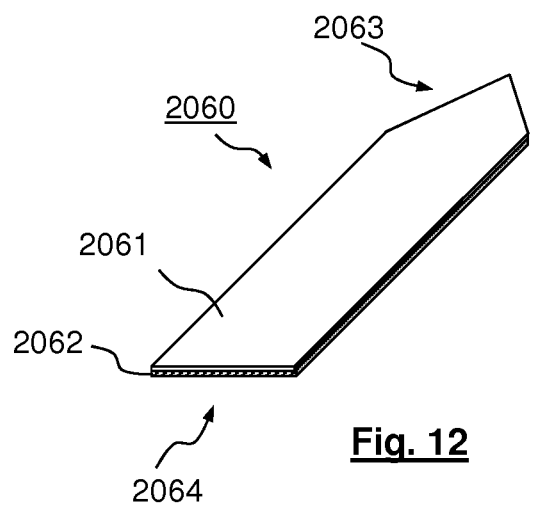
FIG. 12 is a perspective view of the susceptor assembly included in the aerosol-generating device according to FIG. 11.

As can be particularly seen from FIG. 12, the susceptor assembly 2060 of the device 2010 according to FIG. 11 is a bi-layer susceptor blade, very similar to the bi-layer susceptor assembly 120 shown in FIG. 1-3. In contrast to the latter, the distal free end 2063 of the susceptor assembly 2060 is tapered such as to allow the blade-shaped susceptor assembly to readily penetrate into the aerosol-forming substrate 2130 within at the distal end of the aerosol-generating article 2100.

Apart that, the susceptor assembly 2060 and the heating assembly 2005 of the aerosol-generating system 2001 according to FIG. 11 shows the same resistance-over-temperature profile as the aerosol-generating system of FIG. 1, that is, the profile shown in FIG. 4.

Figure 13:
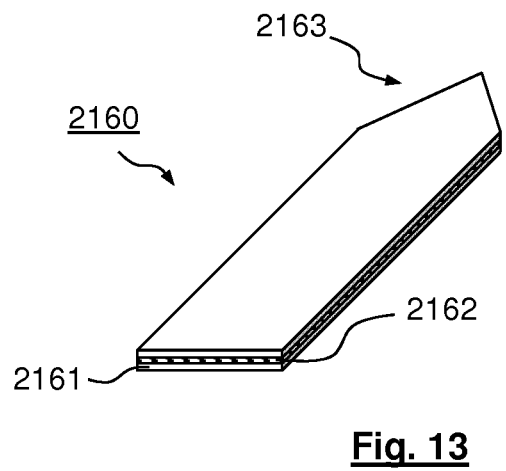
FIG. 13-15 show alternative embodiments of a susceptor assembly for use with the device according to FIG. 11.
Figure 14:
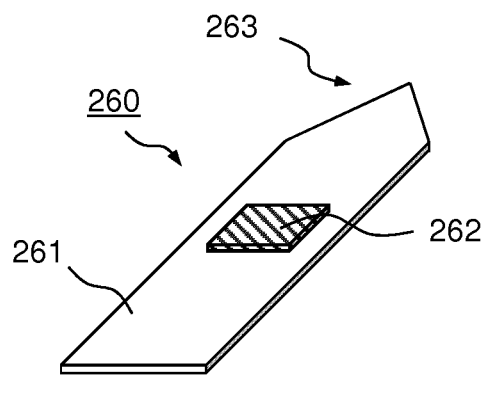
Figure 15:
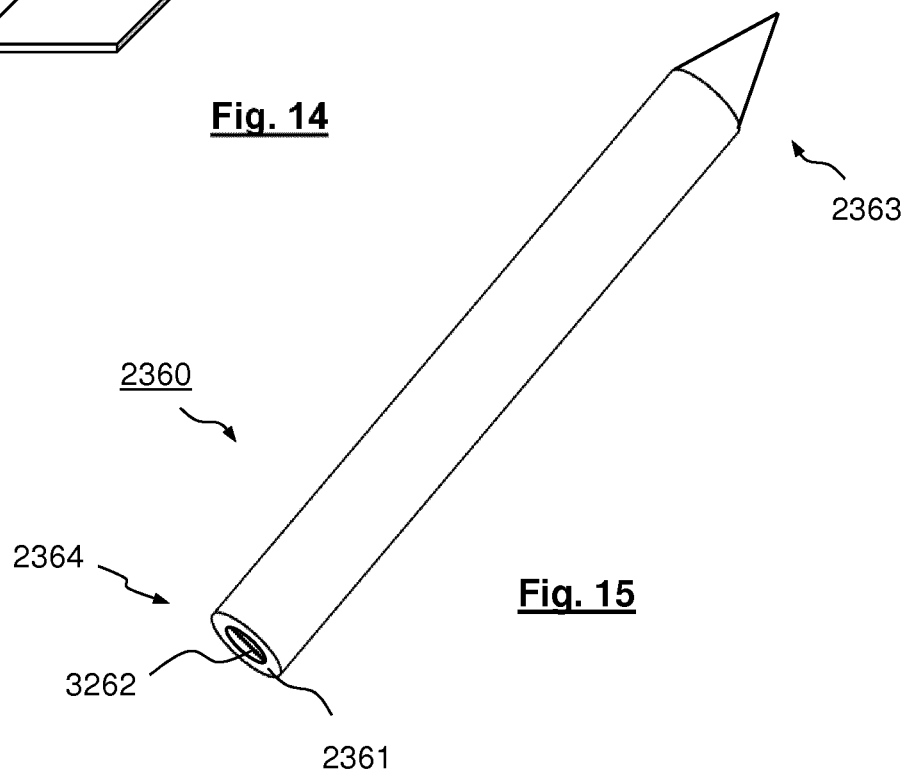

FIG. 13, FIG. 14 and FIG. 15 show further embodiments of susceptor assemblies 2160, 2260, 2360 according to the present invention which may be alternatively used with the device according to FIG. 11. The susceptor assemblies 2160, 2260 and 360 basically correspond to the susceptor assemblies 220, 320 and 1020 shown in FIG. 5, FIG. 6 and FIG. 7, respectively. Hence, most of the features and advantages of these susceptor assemblies 2160, 2260, 2360 have been described with regard to the susceptor assemblies 220, 320, 1020 and will therefore not be repeated. Like the susceptor assembly 120, the respective distal free end 2163, 2263, 2361 of the susceptor assemblies 2160, 2260, 2360 is tapered to facilitate penetration into the aerosol-forming substrate.

Figure 16:
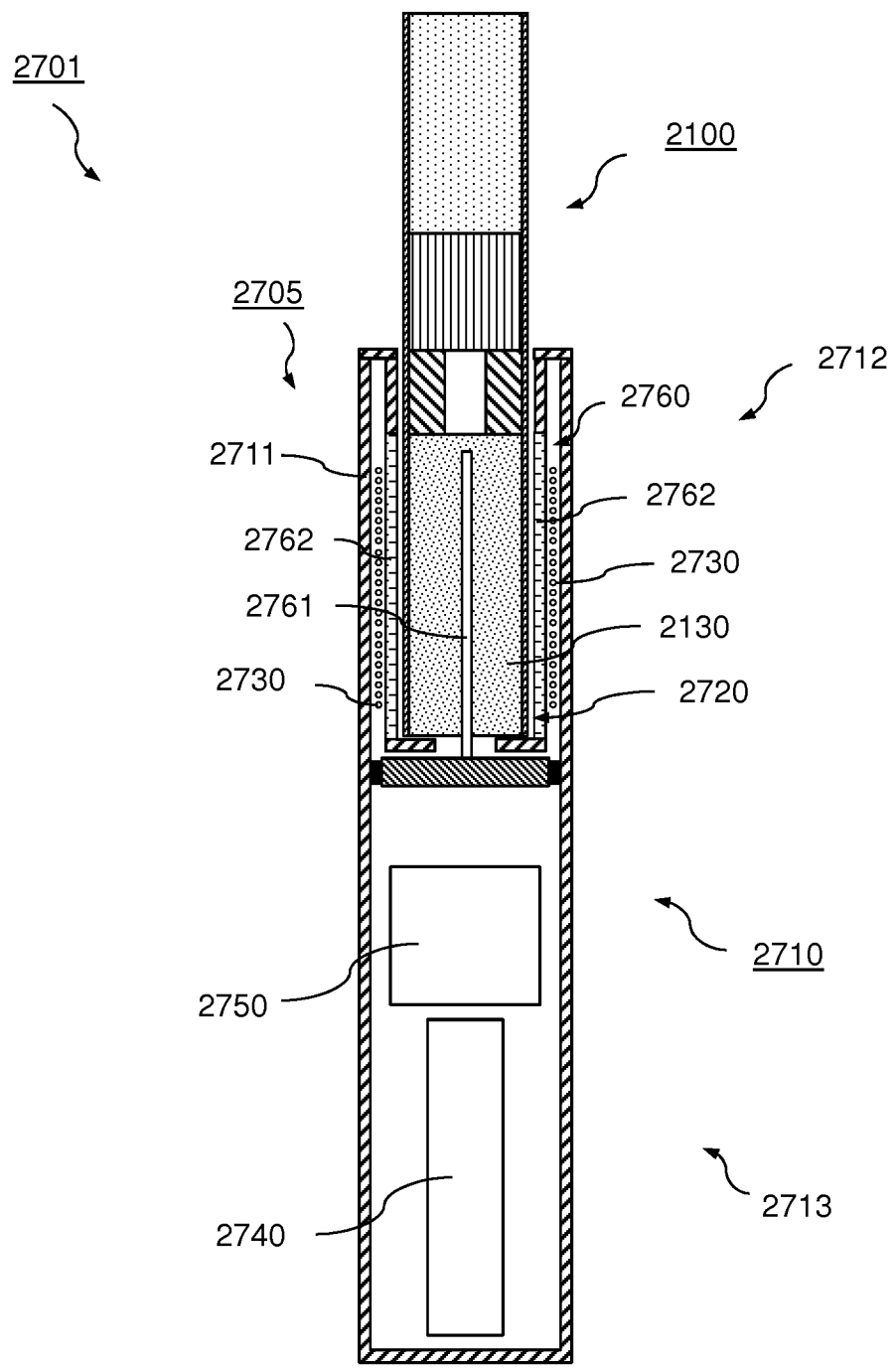
FIG. 16 is a schematic illustration of an aerosol-generating system comprising a heating assembly according to a third exemplary embodiment of the present invention.
Figure 17:
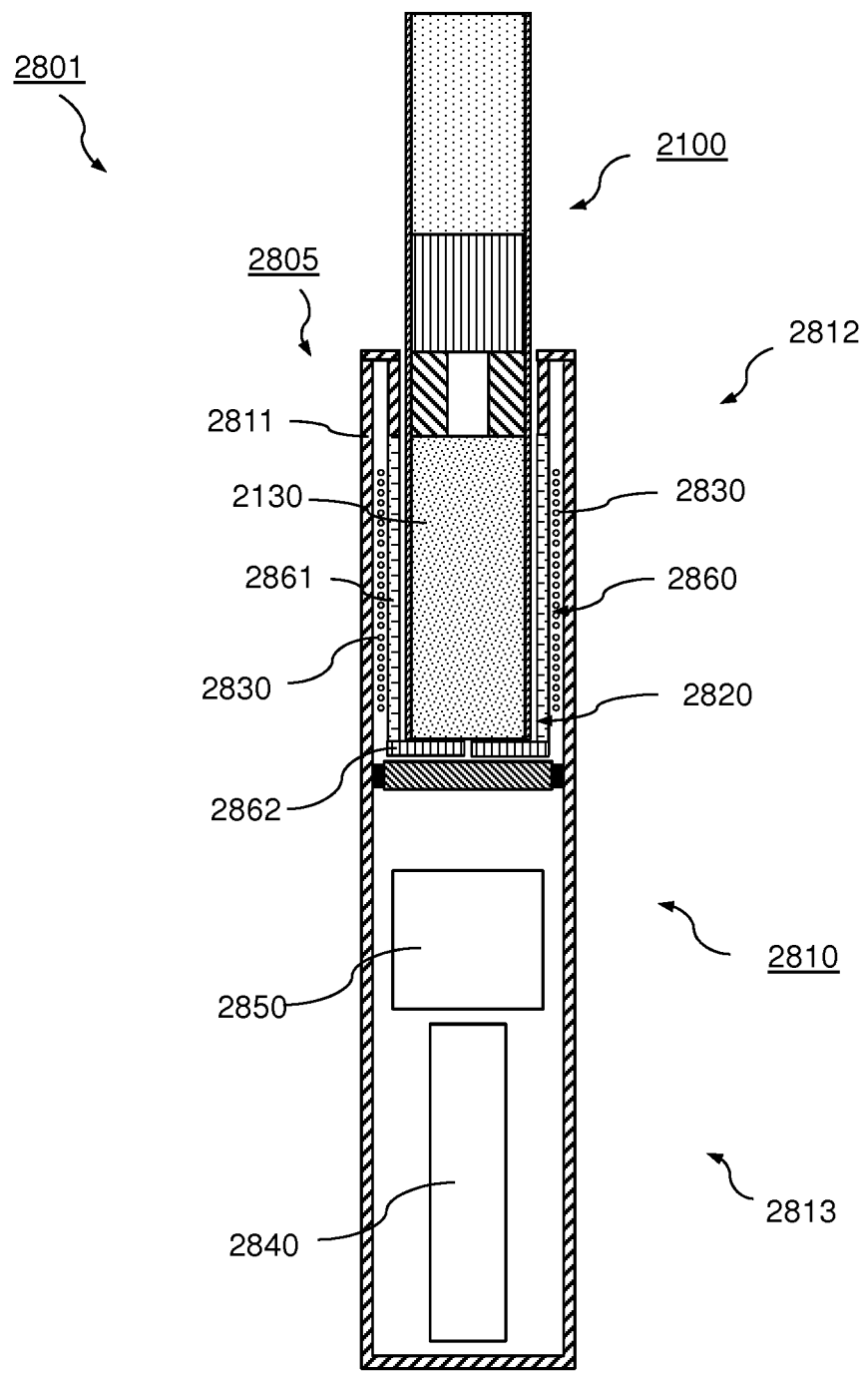
FIG. 17 is a schematic illustration of an aerosol-generating system comprising a heating assembly according to a fourth exemplary embodiment of the present invention.
Figure 18:
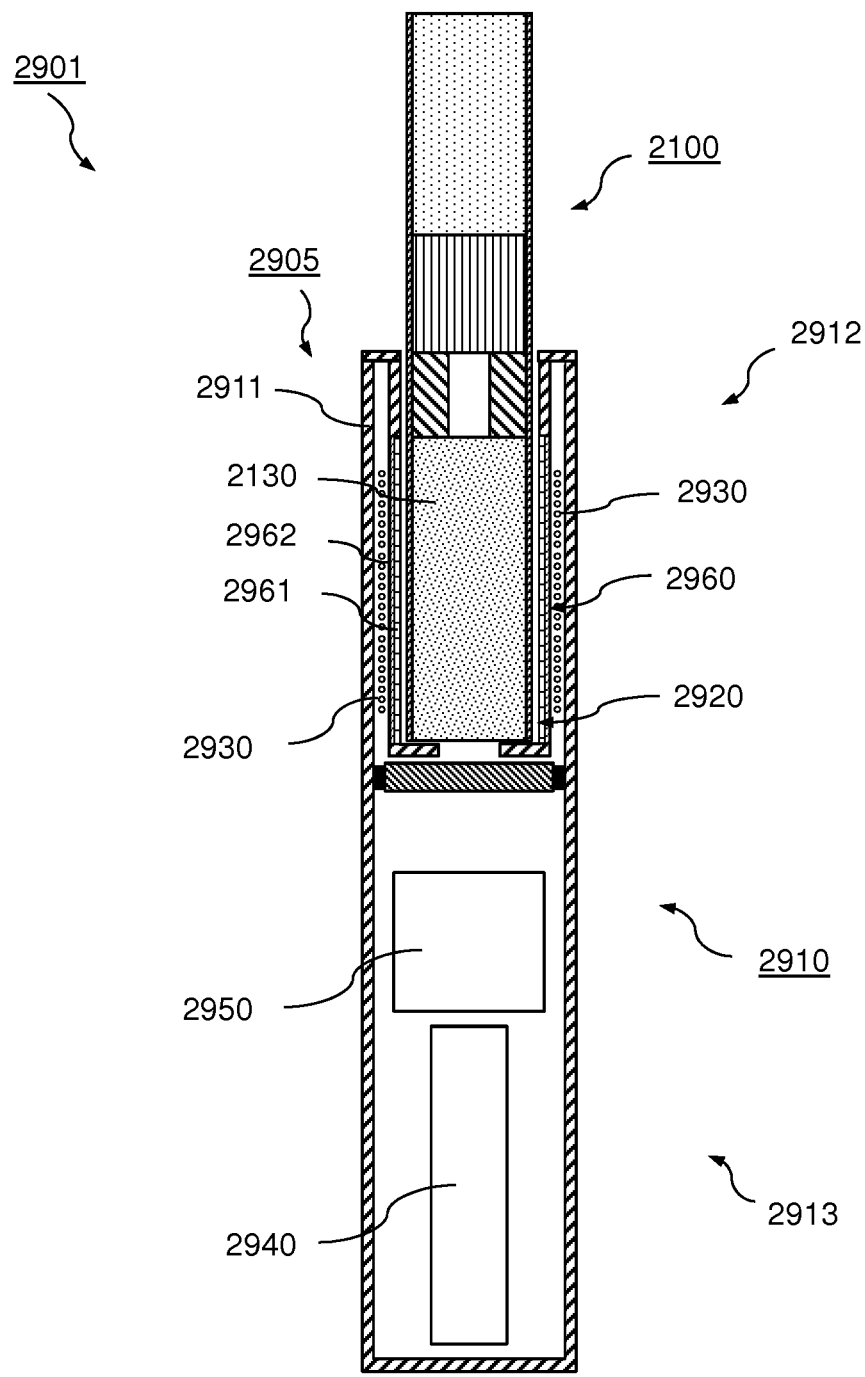
FIG. 18 is a schematic illustration of an aerosol-generating system comprising a heating assembly according to a fifth exemplary embodiment of the present invention.

FIG. 16-18 schematically illustrate further embodiments of aerosol-generating systems 2701, 2801, 2901 at the present invention, in which the respective inductive heating assembly 2705, 2805, 2905 is exclusively part of the respective aerosol-generating device 2710, 2810, 2910. The systems 2701, 2801 and 2901 are very similar to the system 2001 shown in FIG. 11, in particular with regard to the general setup of the devices 2710, 2810, 2910 and the articles 2700, 2800, 2900. Therefore, like or identical features of the devices are denoted with the same reference numerals as in FIG. 11, incremented by 700, 800 and 900, respectively.

In contrast to the device 2010 shown in FIG. 11, the aerosol-generating device 2710 of the aerosol-generating system 2701 according to FIG. 16 comprises a susceptor assembly 2760, in which the first susceptor 2761 and the second susceptor 2762 are of different geometrical configurations. The first susceptor 2761 is a single-layer susceptor blade similar to the bi-layer susceptor assembly 2060 shown in FIG. 11 and FIG. 12, yet without a second susceptor layer. In this configuration, the first susceptor 1761 basically forms an inductive heating blade as it mainly has a heating function. In contrast, the second susceptor 2762 is a susceptor sleeve which forms at least a portion of a circumferential inner side wall of the receiving cavity 2720. Of course, the opposite configuration is also possible in which the first susceptor may be a susceptor sleeve forming at least a portion of a circumferential inner side wall of the cylindrical receiving cavity 2720, whereas the second susceptor may be a single-layer susceptor blade to be inserted into the aerosol-forming substrate. In the latter configuration, the first susceptor may realize an inductive oven heater or heating chamber. In either of these configurations, the first and second susceptor 2761, 2762 are located at different places within the aerosol-generating device 2710, spaced apart from each other but still in thermal proximity to each other.

The aerosol-generating device 2810 of the aerosol-generating system 2801 shown in FIG. 17 comprises a susceptor assembly 2860 which is a susceptor cup, thus realizing an inductive oven heater or heating chamber. In this configuration, the first susceptor 2861 is a susceptor sleeve forming circumferential side wall of the cup-shaped susceptor assembly 2860 and thus at least a portion of the inner side wall of the cylindrical receiving cavity 2820. In contrast, the second susceptor 2862 forms a bottom portion of the cup-shaped susceptor assembly 2860. Both, the first and the second susceptor 2861, 2862 are in thermal proximity to the aerosol-forming substrate 2130 of the aerosol-generating article 2100 when it is received in the receiving cavity 2820 of the device 2810.

The aerosol-generating device 2910 of the aerosol-generating system 2901 shown in FIG. 18 comprises a susceptor assembly 2960 which is a multi-layer susceptor sleeve. In this configuration, the second susceptor 2962 forms an outer wall of the multi-layer susceptor sleeve, whereas the first susceptor 2961 forms an inner wall of the multi-layer susceptor sleeve. This specific arrangement of the first and second susceptor 2961, 2962 is preferred because thus the first susceptor 2961—being primarily used for heating the aerosol-forming substrate 2130—is closer to the substrate 2130. Advantageously, the susceptor assembly 2960 also realizes an inductive oven heater or heating chamber.

Figure 19:
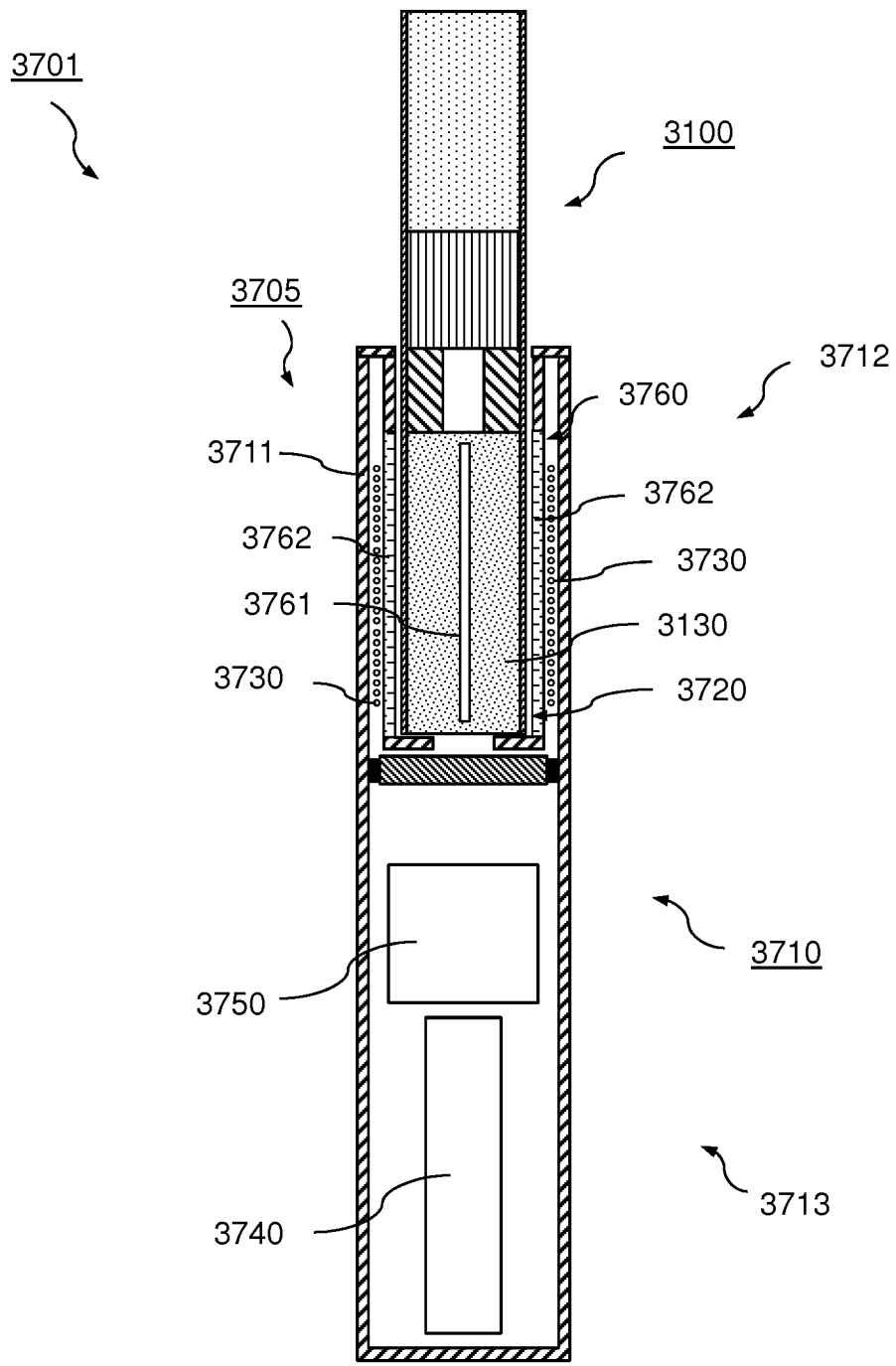
FIG. 19 is a schematic illustration of an aerosol-generating system comprising a heating assembly according to a sixth exemplary embodiment of the present invention.

FIG. 19 schematically illustrates a yet another embodiment of an aerosol-generating system 3701 according to the present invention. The system 3701 is very similar to the system 2701 shown in FIG. 16. Therefore, like or identical features are denoted with the same reference numerals as in FIG. 16, yet incremented by 1000. In contrast to the embodiment shown in FIG. 16, the susceptor assembly 3760 of the heating assembly 3705 according to the embodiment of FIG. 16 is split. While the first susceptor 3761 of the susceptor assembly 3760 is part of the aerosol-generating article 3100, the second susceptor 3762 of the susceptor assembly 3760 is part of the aerosol-generating device 3710. The first susceptor 3761 is a single-layer susceptor strip similar to the bi-layer susceptor assembly 120 shown in FIG. 1-3, yet arranged within the aerosol-forming substrate 3130 of the article 3100 and without a second susceptor layer. Thus, the first susceptor 1761 basically forms an inductive heating element as integral part of the article 3100. The second susceptor 2762 is a susceptor sleeve which forms at least a portion of a circumferential inner side wall of the receiving cavity 2720 realizes an inductive oven heater or heating chamber. Though spaced apart from the first susceptor 3761, the second susceptor 3762 is still in thermal proximity to the first susceptor 3761 and the aerosol-forming substrate 3130, and thus may be readily used as temperature marker.

With regard to all three embodiments shown in FIG. 16-19, the first susceptor preferably is made of ferromagnetic stainless steel which is optimized for heating the aerosol-forming substrate. In contrast, the second susceptor preferably is made of mu-metal or permalloy which is a suitable temperature marker material.

The invention claimed is:

1. An inductive heating assembly configured to inductively heat an aerosol-forming substrate to a pre-determined operating temperature, the heating assembly comprising:
   an induction source configured to generate an alternating electromagnetic field; and
   a susceptor assembly configured to inductively heat the aerosol-forming substrate under influence of the alternating magnetic field generated by the induction source, the susceptor assembly comprising a first susceptor comprising a first susceptor material and a second susceptor comprising a second susceptor material having a Curie temperature at least 50 degrees Celsius below an operating temperature of the heating assembly.

2. The heating assembly according to claim 1, wherein the pre-determined operating temperature is at least 300 degrees Celsius.

3. The heating assembly according to claim 1, wherein the pre-determined operating temperature is at least 400 degrees Celsius.

4. The heating assembly according to claim 1, wherein the second susceptor material has a Curie temperature of at least 100 degrees Celsius below the operating temperature.

5. The heating assembly according to claim 1, wherein the second susceptor material has a Curie temperature of at least 200 degrees Celsius below the operating temperature.

6. The heating assembly according to claim 1, wherein the second susceptor material has a Curie temperature below 350 degrees Celsius.

7. The heating assembly according to claim 1, wherein the second susceptor material has a Curie temperature below 200 degrees Celsius.

8. The heating assembly according to claim 1, wherein the second susceptor comprises one of mu-metal or permalloy.

9. The heating assembly according to claim 1, wherein the first susceptor material is electrically conductive and/or one of paramagnetic, ferromagnetic, or ferrimagnetic.

10. The heating assembly according to claim 1, wherein the first susceptor material comprises one of aluminum, iron, nickel, copper, bronze, cobalt, plain-carbon steel, stainless steel, ferritic stainless steel, martensitic stainless steel, or austenitic stainless steel.

11. The heating assembly according to claim 1,
   wherein the first susceptor material has a positive temperature coefficient of resistance, and
   wherein the second susceptor material has a negative temperature coefficient of resistance.

12. The heating assembly according to claim 1, wherein the first susceptor and the second susceptor are in intimate physical contact with each other.

13. The heating assembly according to claim 1, wherein the first susceptor or the second susceptor or both the first and the second susceptor, or the entire susceptor assembly, is one of a particulate susceptor, or a susceptor filament, or a susceptor mesh, or a susceptor wick, or a susceptor pin, or a susceptor rod, or a susceptor blade, or a susceptor strip, or a susceptor sleeve, or a susceptor cup, or a cylindrical susceptor, or a planar susceptor.

14. The heating assembly according to claim 1, further comprising a controller operatively connected to the induction source and configured to control operation of the induction source and to control heating of the aerosol-forming substrate to the pre-determined operating temperature.

15. The heating assembly according to claim 14, wherein the controller is further configured to control operation of the induction source in a closed-loop configuration.

16. The heating assembly according to claim 14, wherein the controller is further configured to determine, during preheating of the heating assembly starting at room temperature towards the pre-determined operating temperature, a minimum value of an apparent resistance occurring in a temperature range of ±5 degrees Celsius around a Curie temperature of the second susceptor material.

17. The heating assembly according to claim 1, further comprising a DC power supply configured to provide a DC supply voltage and a DC supply current to the induction source.

18. An aerosol-generating device for generating an aerosol by heating an aerosol-forming substrate, the device comprising:

a receiving cavity configured to receive the aerosol-forming substrate to be heated; and an inductive heating assembly according to claim 1 configured to inductively heat the aerosol-forming substrate within the receiving cavity.

19. An aerosol-generating system comprising an aerosol-generating device, an aerosol-generating article for the aerosol-generating device, and an inductive heating assembly according to claim 1, wherein the induction source of the heating assembly is part of the aerosol-generating device, wherein the first susceptor of the susceptor assembly is part of the aerosol-generating article, and wherein the second susceptor of the susceptor assembly is part of the aerosol-generating article or part of the aerosol-generating device.

* * * * *